(12) United States Patent
Jensen et al.

(10) Patent No.: US 8,083,704 B2
(45) Date of Patent: *Dec. 27, 2011

(54) SYSTEMS AND METHODS FOR OFF-WEIGHTING A LIMB

(75) Inventors: Jeffrey Jensen, Evergreen, CO (US); William O. Reid, Jr., Longmont, CO (US)

(73) Assignee: Medefficiency, Inc., Wheat Ridge, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/690,895

(22) Filed: Jan. 20, 2010

(65) Prior Publication Data

US 2010/0130902 A1    May 27, 2010

Related U.S. Application Data

(63) Continuation of application No. 11/082,388, filed on Mar. 16, 2005, now Pat. No. 7,666,155.

(60) Provisional application No. 60/554,093, filed on Mar. 17, 2004.

(51) Int. Cl.
   *A61F 5/00* (2006.01)

(52) U.S. Cl. .......................................... 602/23; 602/27

(58) Field of Classification Search .............. 602/23–30; 128/882
   See application file for complete search history.

(56) References Cited

U.S. PATENT DOCUMENTS

| | | | |
|---|---|---|---|
| 2,516,872 A * | 8/1950 | Hauser et al. ................... 602/27 |
| 3,083,708 A | 4/1963 | Gottfried |
| 3,338,237 A | 8/1967 | Sconce |
| 3,351,055 A | 11/1967 | Gottfried |
| 3,580,248 A | 5/1971 | Larson |
| 3,701,349 A | 10/1972 | Larson |
| 3,760,056 A | 9/1973 | Rudy |
| 3,811,434 A | 5/1974 | Jacobson et al. |
| 3,955,565 A | 5/1976 | Johnson, Jr. |
| 4,076,022 A | 2/1978 | Walker |
| 4,320,748 A | 3/1982 | Racette et al. |
| 4,454,871 A | 6/1984 | Mann et al. |
| 4,502,470 A | 3/1985 | Kiser et al. |
| 4,641,639 A | 2/1987 | Padilla |
| 4,693,239 A | 9/1987 | Clover, Jr. |
| 4,727,865 A | 3/1988 | Hill-Byrne |
| 4,805,601 A | 2/1989 | Eischen, Sr. |
| 4,844,094 A | 7/1989 | Grim |
| 4,869,267 A | 9/1989 | Grim et al. |
| 4,913,755 A | 4/1990 | Grim |
| 4,964,402 A | 10/1990 | Grim et al. |
| 4,996,979 A | 3/1991 | Grim et al. |
| 5,014,690 A * | 5/1991 | Hepburn et al. ................. 602/16 |

(Continued)

*Primary Examiner* — Michael A. Brown
(74) *Attorney, Agent, or Firm* — Faegre & Benson LLP

(57) ABSTRACT

Embodiments of the present invention provide a system for limb off-weighting, including a sleeve operable to wrap at least partially around a leg, a support strut coupled to the sleeve to receive weight applied to the sleeve, and a foot assembly configured to support and protect the bottom of a foot, wherein the foot assembly is coupled to the support strut and operable to receive weight applied to the sleeve and transfer the weight to underlying surfaces, thus off-weighting and reducing pressure and shearing forces on the foot and ankle. According to some embodiments, foot assembly pivots around the support strut providing an assembled mode and a storage mode. According to other embodiments, sleeve is an open-ended conical shape. According to various other embodiments, the support strut may be tilted to accommodate legs and/or calves of varying sizes, and the foot assembly may adjust to feet of varying sizes.

17 Claims, 33 Drawing Sheets

U.S. PATENT DOCUMENTS

| | | | | |
|---|---|---|---|---|
| 5,027,801 | A | 7/1991 | Grim | |
| 5,078,128 | A | 1/1992 | Grim et al. | |
| 5,088,481 | A | 2/1992 | Darby | |
| 5,125,400 | A | 6/1992 | Johnson, Jr. | |
| 5,139,475 | A | 8/1992 | Robicsek | |
| 5,197,942 | A | 3/1993 | Brady | |
| 5,218,954 | A | 6/1993 | van Bemmelen | |
| 5,226,245 | A | 7/1993 | Lamont | |
| 5,277,695 | A | 1/1994 | Johnson, Jr. et al. | |
| RE34,661 | E | 7/1994 | Grim | |
| 5,329,705 | A | 7/1994 | Grim et al. | |
| 5,348,530 | A | 9/1994 | Grim et al. | |
| 5,354,260 | A | 10/1994 | Cook | |
| 5,370,133 | A | 12/1994 | Darby et al. | |
| 5,378,223 | A | 1/1995 | Grim et al. | |
| 5,389,065 | A | 2/1995 | Johnson, Jr. | |
| 5,399,152 | A | 3/1995 | Habermeyer et al. | |
| 5,403,265 | A | 4/1995 | Berguer et al. | |
| 5,419,757 | A | 5/1995 | Daneshvar | |
| 5,421,874 | A | 6/1995 | Pearce | |
| 5,435,009 | A | 7/1995 | Schild et al. | |
| 5,453,082 | A | 9/1995 | Lamont | |
| 5,464,385 | A * | 11/1995 | Grim | 602/27 |
| 5,466,250 | A | 11/1995 | Johnson, Jr. et al. | |
| 5,503,622 | A | 4/1996 | Wehr | |
| 5,520,628 | A | 5/1996 | Wehr | |
| 5,527,269 | A | 6/1996 | Reithofer | |
| 5,571,077 | A | 11/1996 | Klearman et al. | |
| 5,577,998 | A | 11/1996 | Johnson, Jr. et al. | |
| 5,605,535 | A | 2/1997 | Lepage | |
| 5,609,570 | A | 3/1997 | Lamont | |
| 5,620,411 | A | 4/1997 | Schumann et al. | |
| 5,665,059 | A | 9/1997 | Klearman et al. | |
| 5,761,834 | A | 6/1998 | Grim et al. | |
| 5,778,565 | A | 7/1998 | Holt et al. | |
| 5,792,084 | A | 8/1998 | Wilson et al. | |
| 5,833,639 | A | 11/1998 | Nunes et al. | |
| 5,839,139 | A | 11/1998 | Fink | |
| 5,940,992 | A | 8/1999 | Darby | |
| 6,021,780 | A | 2/2000 | Darby | |
| 6,027,468 | A | 2/2000 | Pick | |
| 6,179,800 | B1 | 1/2001 | Torrens | |
| 6,228,044 | B1 | 5/2001 | Jensen et al. | |
| 6,267,742 | B1 | 7/2001 | Krivosha et al. | |
| 6,409,691 | B1 | 6/2002 | Dakin et al. | |
| 6,485,447 | B1 | 11/2002 | Lavery et al. | |
| 6,547,751 | B1 * | 4/2003 | Barberio | 602/14 |
| 6,572,571 | B2 | 6/2003 | Lowe | |
| 6,682,497 | B2 | 1/2004 | Jensen et al. | |
| 6,976,972 | B2 | 12/2005 | Bradshaw | |
| 7,666,155 | B1 * | 2/2010 | Jensen et al. | 602/23 |
| 2004/0215120 | A1 | 10/2004 | Jensen et al. | |
| 2005/0054962 | A1 | 3/2005 | Bradshaw | |

* cited by examiner

SYSTEMS AND METHODS FOR OFF-WEIGHTING A LIMB

CROSS-REFERENCE TO RELATED APPLICATIONS

This application is a continuation of U.S. patent application Ser. No. 11/082,388, filed on Mar. 16, 2005, which claims the benefit of U.S. Provisional Patent Application Ser. No. 60/554,093, filed on Mar. 17, 2004. The aforementioned applications are incorporated herein by reference in their entireties for all purposes.

STATEMENT REGARDING FEDERALLY-SPONSORED RESEARCH OR DEVELOPMENT

Embodiments of the present invention were made with U.S. Government support, and the U.S. Government may have certain rights in the invention. The U.S. Government's rights in the invention are provided for by the terms of contract numbers DAAH01-03-C-R001 and W31P4Q-04-C-R013, sponsored by the Defense Advanced Research Projects Agency.

BACKGROUND OF THE INVENTION

The present invention relates generally to limb off-weighting and splints utilized for the treatment of injuries to the lower extremities.

Soldiers who suffer trauma to a foot or lower leg on the battlefield must often walk at least a short distance to safety and/or medical treatment. Walking on an injured foot or lower leg may often further compound the injury. Although traditional splint devices provide limited stability, they provide little or no off-weighting capability or portability.

Medical patients who have recently had surgery on a foot or lower leg, as well as medical patients at risk for developing diabetic ulcers or other contact lesions, also benefit from an off-weighting capability that may be administered relatively rapidly. However, current off-weighting devices often require extensive amounts of time to apply, often fail to substantially redirect most or all of the weight placed on a particular foot, often off-weight only a wound area and not the entire foot, and may cause discomfort even when weight is not placed on the devices.

Athletes and outdoor enthusiasts, in both emergency and non-emergency situations, and with both acute and chronic injuries, may benefit by redistributing weight and relieving pressure on injured areas of the leg, foot, and/or ankle. Therefore, there is a need for improved systems and methods for limb off-weighting.

BRIEF SUMMARY OF THE INVENTION

Embodiments of the present invention relate generally to limb off-weighting and splints utilized for the treatment of injuries to the lower extremities.

Some embodiments of the present invention provide systems for limb off-weighting to reduce pressure and shear stress, including a sleeve operable to wrap at least partially around a leg, a support strut coupled to a side of the sleeve and operable to receive weight applied to the sleeve, and a foot assembly configured to support and/or constrain a bottom of a foot, wherein the foot assembly is coupled to the support strut and operable to receive the weight applied to the sleeve and transfer the weight to an underlying surface. According to some instances of the embodiments, the sleeve is coupled to the support strut via a sleeve attachment; further, the sleeve may be coupled to the sleeve attachment via a hook-and-loop closure.

In some cases, the foot assembly comprises a semi-circular strut pocket, and a bottom end of the support strut is semi-circular and configured to interface with the strut pocket to allow the support strut to pivot towards or away from the leg to accommodate legs of varying diameters. In other cases, the foot assembly is pivotably coupled to the support strut such that the foot assembly extends substantially perpendicularly from the support strut in an operational mode and rotates about a pivot until the foot assembly extends substantially parallel to the support strut in a storage mode. In yet other cases, the foot assembly is pivotably coupled to the support strut via a strut pivot, the strut pivot includes a pin, and the foot assembly includes a pivot clip configured to attach to the pin.

According to yet other instances of the embodiments, the support strut is extendable. In some cases, the support strut comprises an inner strut and an outer strut, and the inner strut is slidably coupled to the outer strut via a strut latch. The strut latch may substantially prevent the inner strut from sliding relative to the outer strut in a closed position, and the strut latch may allow the inner strut to slide relative to the outer strut in an open position. In addition, the strut latch may open and close via a latch lever configured to translate a rotational motion into a substantially linear motion. In other cases, the inner strut is coupled to the sleeve and the outer strut is coupled to the foot assembly. In yet other cases, the support strut includes a cylindrical inner strut and a tubular outer strut, the cylindrical inner strut having a tooth extending from a portion of its diameter, the tubular outer strut having axially-spaced grooves formed around a portion of its inner diameter, such that the cylindrical inner strut slides relative to the tubular outer strut until the cylindrical inner strut is twisted causing the tooth to be inserted into one of the axially-spaced grooves.

In some cases, the support strut is retractable, the sleeve forms an open-ended conical shape, or the sleeve is tailored for attachment to an area of the human body selected from the group consisting of: a thigh area and a calf area. In other cases, the foot assembly provides traction during ambulation. In yet other cases, the systems further include a heel support or a foot pad. The foot assembly may include an extender selected from the group consisting of a heel extender and a toe extender. The sleeve may comprise a bladder with chambers filled with air or other conformable material, wherein the conformable material may harden following application of the sleeve to the leg. In some instances, the sleeve is perforated with a plurality of vent holes to improve air circulation for moisture and temperature management.

Some embodiments of the present invention provide methods of applying an off-weighting device, the method including wrapping a sleeve conically around a calf of a leg with a top edge of the sleeve substantially near a widest portion of the calf, providing an off-weighting device having two extendable support struts coupled to a foot assembly, placing a foot of the leg in the foot assembly, extending the two extendable support struts until the two extendable support struts reach above or approximately level with the top edge of the sleeve, locking the two extendable support struts in place; and attaching the sleeve to the two extendable support struts, such that a weight applied to the sleeve is redirected through the two extendable support struts and through the foot assembly to off-weight at least a portion of the foot and to reduce shear forces experienced during ambulation.

Some embodiments of the present invention provide systems for limb off-weighting, the systems including a sleeve operable to wrap at least partially around a leg, a rigid boot structure configured to attach to the sleeve and to wrap around at least a portion of the leg, and a foot assembly including foam padding, wherein the foot assembly is coupled to the rigid boot structure and configured to at least partially off-weight a foot and an ankle of the leg by directing weight applied to the sleeve into the foot assembly instead of through the foot.

Some embodiments of the present invention provide systems for limb off-weighting, the systems including a sleeve operable to wrap at least partially around a limb, a support strut coupled to a side of the sleeve and operable to receive force applied to the sleeve, and a support assembly configured to support an end of the limb, wherein the support assembly is coupled to the support strut and operable to receive the force applied to the sleeve and to substantially transfer the force to an underlying surface through the support assembly rather than through the end of the limb.

This summary provides only a general outline of some embodiments of the present invention. Many other objects, features, advantages and other embodiments of the present invention will become more fully apparent from the following detailed description, the appended claims and the accompanying drawings.

BRIEF DESCRIPTION OF THE SEVERAL VIEWS OF THE DRAWING

A further understanding of the various embodiments of the present invention may be realized by reference to the figures which are described in remaining portions of the specification. In the figures, like reference numerals are used throughout several to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION OF THE INVENTION

Some embodiments of the present invention provide a limb off-weighting device operable for the treatment of injuries to the lower extremities of the foot or ankle, and in some cases to injuries of the tibia, knee and femur. Further, the limb off-weighting device can be used to modify the location of weight bearing associated with an extremity. Thus, for example, weight bearing can be transferred from the foot to the calf area, or from the foot and apportioned between the calf and thigh areas. The off-weighting device may include a conformable sleeve, collapsible support struts, a foot assembly, and tread. In some cases, the device is adjustable to fit a multitude of patient leg sizes and/or body weights. The device directs the load bearing for the body from the leg into the struts and then the foot plate and thereby removes weight from the foot. This allows for self-ambulation of the patient from the location where the injury occurred to a medical care facility. In some cases, the device can be either self-applied or applied by a single caregiver and would be used in emergency situations such as military combat or for remote wilderness areas. In other cases, the device is applied in a physician's office, and re-applied periodically to adjust for various changes.

Embodiments of the device may also serve as a substitute for, or as a portable or cost-effective alternative to, a total contact cast, and may provide a higher degree of off-weighting capability than a total contact cast, such as, for example, embodiments of the total contact cast described in U.S. patent application Ser. No. 10/422,621, filed on Apr. 24, 2003 and entitled "Apparatus and Method for Applying a Total Contact Cast;" such application is hereby incorporated by reference herein in its entirety for all purposes. For example, embodiments of such a total contact cast may off-weight a leg by approximately thirty to forty percent. By comparison, embodiments of the present invention may off-weight a leg by approximately seventy-five percent or more. In addition, embodiments of the present invention off-weight the entire bottom of the foot, instead of just off-weighting a wound site.

Systems and methods according to embodiments of the present invention are described using one or more terms as set forth below. In particular, as used herein, the term "coupled" is used in its broadest sense to mean attached, affixed, joined, or connected, either indirectly via another element, or directly. "Rotatably coupled" means coupled in a way that permits rotation. "Slidably coupled" means coupled in a way that permits sliding. As used herein, to "off-weight" means to reduce or relieve weight normally applied to a part of the body; for example, to off-weight a foot means to reduce or relieve weight normally experienced by the foot by redirecting force applied by the leg through an alternate path.

Figure 1:
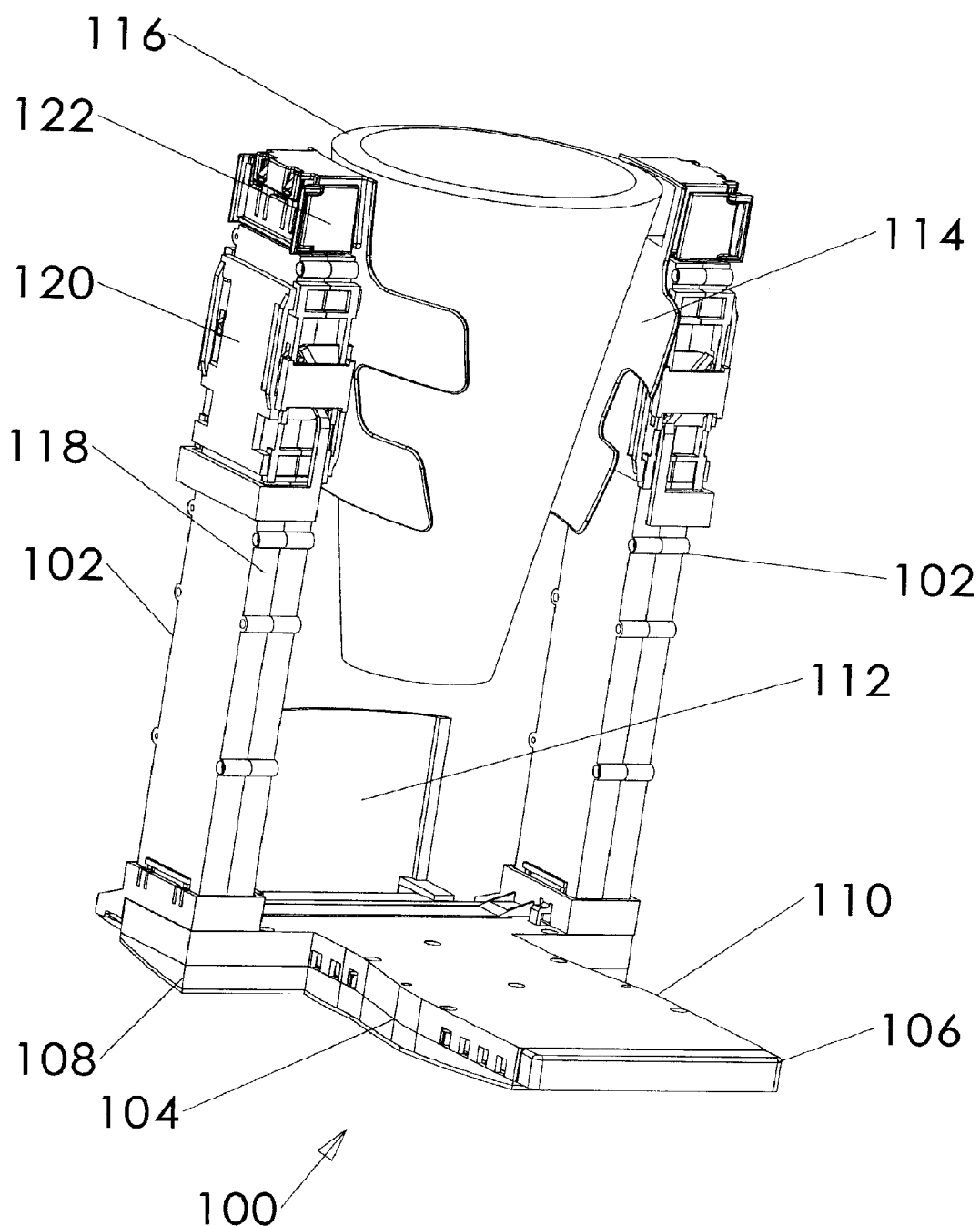
FIG. 1 illustrates an isometric view of an off-weighting device in an assembled position according to some embodiments of the present invention.

Turning now to FIG. 1, an off-weighting device 100 in an assembled position according to some embodiments of the present invention is provided. Off-weighting device 100 may include a sleeve 116, one or more support struts 102, one or more sleeve attachments 114, and a foot assembly 104. Foot assembly 104 may include a foot plate 110 and a stiffener 108, a toe extender 106, and a heel support 112. Support struts 102 may be extendable, and may include an outer strut 118 and an inner strut 122; the outer and inner struts 118, 122 may be coupled via a strut latch 120. Sleeve attachments 114 clip onto struts 102 and may attach to sleeve 116 via a hook-and-loop fastener system.

Foot assembly 104 may pivot and/or rotate with respect to struts 102. For example, foot assembly 104 may be rotated to the collapsed or folded position of off-weighting device 100 depicted in FIG. 2. Support struts 102 may be coupled to foot assembly 104 via a strut pivot 202, around which foot assembly 104 rotates. Alternatively, support struts 102 may be coupled to foot assembly 104 directly via a pivotable hook and hinge type joint such as those found on strut pivot 202. Foot assembly 104 may rotate approximately 270 degrees from the assembled position of FIG. 1 into the collapsed or folded position of FIG. 2. According to other embodiments or the present invention, foot assembly 104 may rotate approximately 90 degrees into an alternative collapsed or folded position. This ability of off-weighting device 100 to fold or collapse permits off-weighting device 100 to be easily stored and/or carried to locations where it may be needed, such as in the battlefield or into the outdoors.

Figure 3:
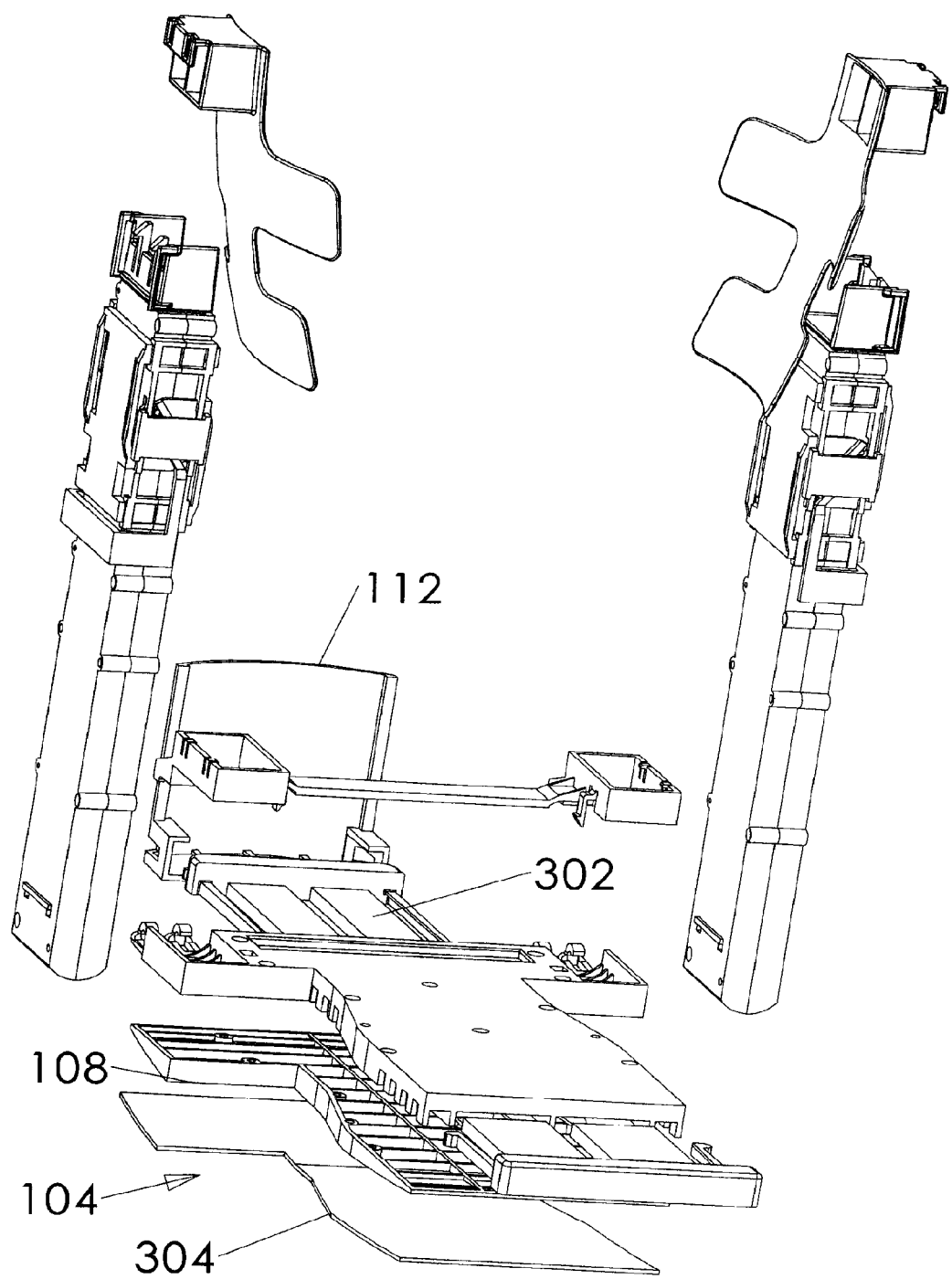
FIG. 3 illustrates an exploded isometric view of an off-weighting device without a sleeve according to some embodiments of the present invention.

Turning now to FIG. 3, an exploded isometric view of an off-weighting device according to some embodiments of the present invention is provided. As depicted, for example, in FIG. 3, foot assembly 104 may further include a heel extender 302 to which heel support 112 is coupled, and a tread 304 applied to an underside of stiffener 108.

Figure 4A:
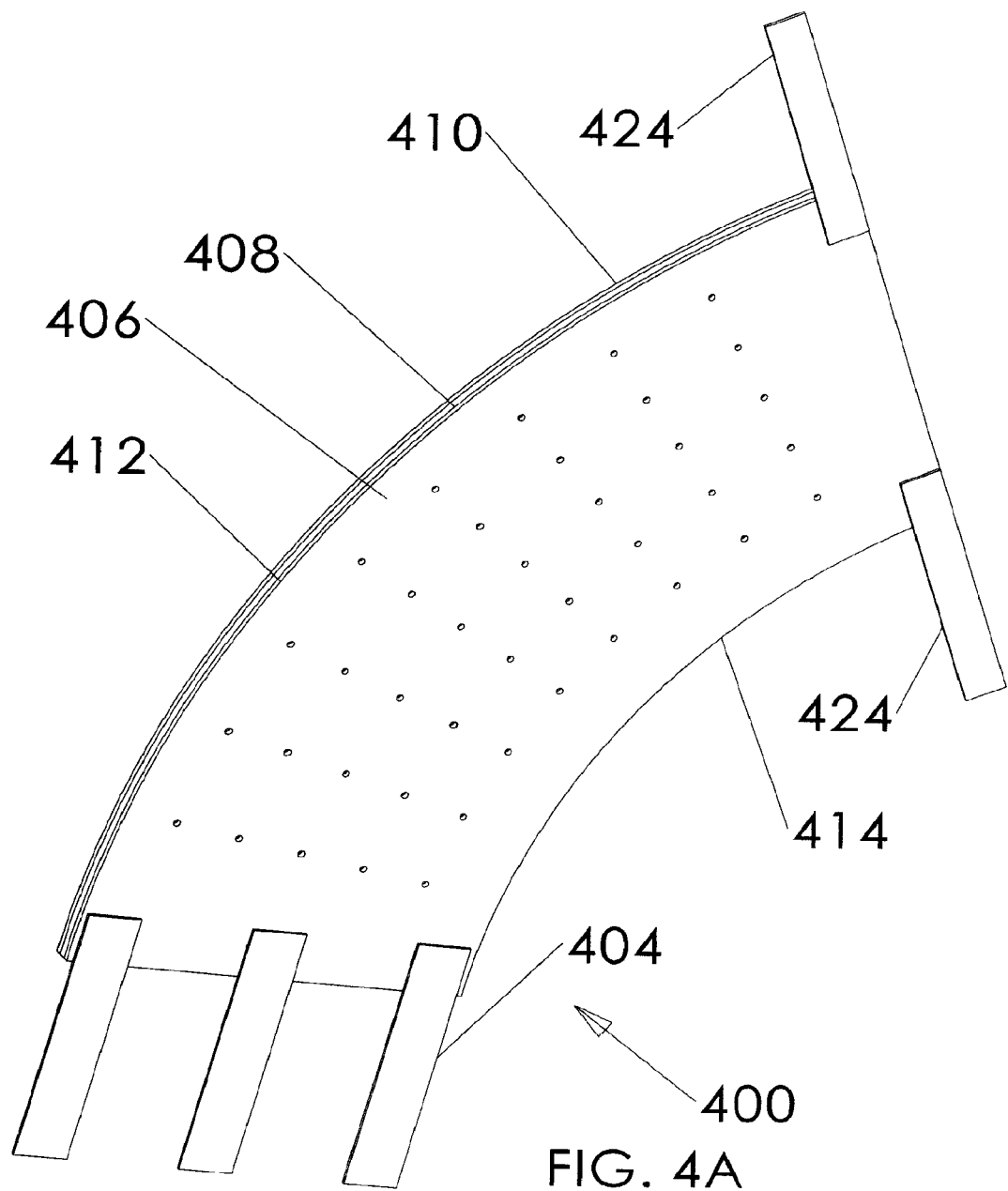
FIG. 4A illustrates an isometric view of a one-size-fits-all sleeve for an off-weighting device according to some embodiments of the present invention.

In a typical scenario, a user who wishes to off-weight a foot due to injury or diabetic ulceration, for example, applies sleeve 116 to an area of the leg, such as, for example, to a calf. FIG. 4A illustrates a one-size-fits-all sleeve 400 for an off-weighting device 100 according to some embodiments of the present invention. Straps 404 with hook-and-loop fasteners may be integral to sleeve 400; for example, straps 404 may be sewn onto sleeve 400. Reclosable fasteners 404, such as hook and loop tape, are used to secure sleeve 400 to itself after it is wrapped around the leg. Sleeve 400 may be shaped in an open-ended, downward-pointing conical shape, such that a circumference of upper edge 412 of sleeve 400 is larger than a circumference of lower edge 414 of sleeve 400. According to some embodiments of the present invention, the circumference of upper edge 412 is approximately 20.5 inches and the circumference of lower edge 414 is approximately 13.5 inches. According to some embodiments of the present invention, sleeve 400 comprises one or more bladders that may be filled with air or other conformable material which is then wrapped around the leg. This material may harden following application of sleeve 400 to the leg. For example, a silicone material may be injected into a sleeve/bladder 400 and permitted to cure halfway, then the sleeve/bladder 400 may be wrapped around a leg to complete the curing process conforming to the leg.

Bladder/sleeve 400 provides the conforming surface between support struts 102 and the user's leg. This creates the zone of total contact that distributes the load being transferred from the ground into the leg. Through a tapered design, such as an open-ended, downward-pointing conical shape, the pressure on the leg is relieved when the user is not applying load to the leg. This improves the long term comfort of the system. Bladder/sleeve 400 may allow for adjustment and be capable of being customized for each user (medical patient, injured soldier, etc.) at the time of application. Sleeve 400 may also include multiple layers to improve stability, water resistance, and comfort. For example, sleeve 400 may include an inner layer 410 for contacting the skin, a middle layer 408 to provide structural strength, and an outer layer 406 to provide a surface that is hook tape compatible for securing to sleeve attachment 114. According to some embodiments of the present invention, inner layer 410 may be a hydrophilic open celled polyurethane foam layer; middle layer 408 may be a middle foam layer (L800 or T80); and outer layer 406 may be an outer nylon layer. According to some embodiments of the present invention, middle layer 408 carries importance in off-weighting the foot. According to some embodiments of the present invention, the middle layer 408 may be comprised of a closed-cell chemically crosslinked polyethylene foam and other ethylene vinyl acetate foams: two types of this foam are Volteck Minicell L800 and EN Murray T80. The Volteck material may exhibit a greater stiffness than the EN Murray material, but may also exhibit a slightly lower tear strength. These materials are named by way of example and not by way of limitation; various other kinds of materials may be used to form middle layer 408. For example, other types of polyurethane and/or crosslinked polyethylene foams or materials, or their equivalents, may be used. Middle layer 408 may have a nominal thickness of $1/8$ to $3/16$ inch.

Inner layer 410 may be constructed of a hydrophilic open celled polyurethane foam material, and may be approximately $3/16$ inches thick. One type of this foam is Lindell HSSX7 and it may provide a soft feel against the leg and allow moisture from sweat to be wicked away from the leg. Outer layer 406 may be constructed from a nylon backed foam material that is hook compatible. This allows the hook straps being used to close the sleeve to firmly grasp the sleeve. Various other suitable compounds or materials may be used to construct inner layer 410, middle layer 408, and outer layer 406, to provide the desired properties or other beneficial properties. Inner layer 410, middle layer 408, and/or outer layer 406 may be die cut from sheets of larger material. Sleeve 400 may be perforated with several vent holes (as depicted in FIG. 4A) which may allow improved air circulation for management of moisture and temperatures along the leg.

Hook tape straps 404, 420 may be used to secure sleeve 116, 400, 402 to itself Such straps may be sewn to the sleeve. At the end of sleeve 116, 400, 402, opposite of hook tape straps 404, 420, two straps 424, one strap each at the inner and outer radius of sleeve 116, 400, 402 may be sewn to sleeve 116, 400, 402 and extend radially therefrom. Such straps 424 may be used when the sleeve is being applied to assist in pulling the sleeve snugly over the leg. Additionally, a long two inch wide strap may be attached to the center of sleeve 116, 400, 402. This strap is secured following the attachment of sleeve 116, 400, 402, and may be placed over sleeve attachments 114 to provide additional support to ensure the hook tape secures to sleeve 116, 400, 402.

Non-perforated sleeve 400 is one size fits all and adjusts to different sizes of legs through varying the amount of overlap. One possible configuration of sleeve 400 utilizes a minimum radius of 13.5 inches and a maximum radius of 20.5 inches over an arc angle of 60-65 degrees as shown in FIG. 4A. Perforated sleeve 402 adjusts to different leg sizes by being torn or cut to size. Sleeve 402 may be marked or perforated at different locations. If sleeve 402 is being applied to a smaller leg, then the upper portion may be removed. For a larger leg, the lower portion may be removed and for an average size leg, a strip from both the upper and lower portions may be removed. According to some embodiments of the present invention, a one size fits all sleeve 400 may be preferred because it does not require evaluation of the patient's and/or user's leg size or modification of sleeve 400. Holes may be punched into the sleeve material through all layers to allow for better ventilation and moisture control.

Figure 4B:
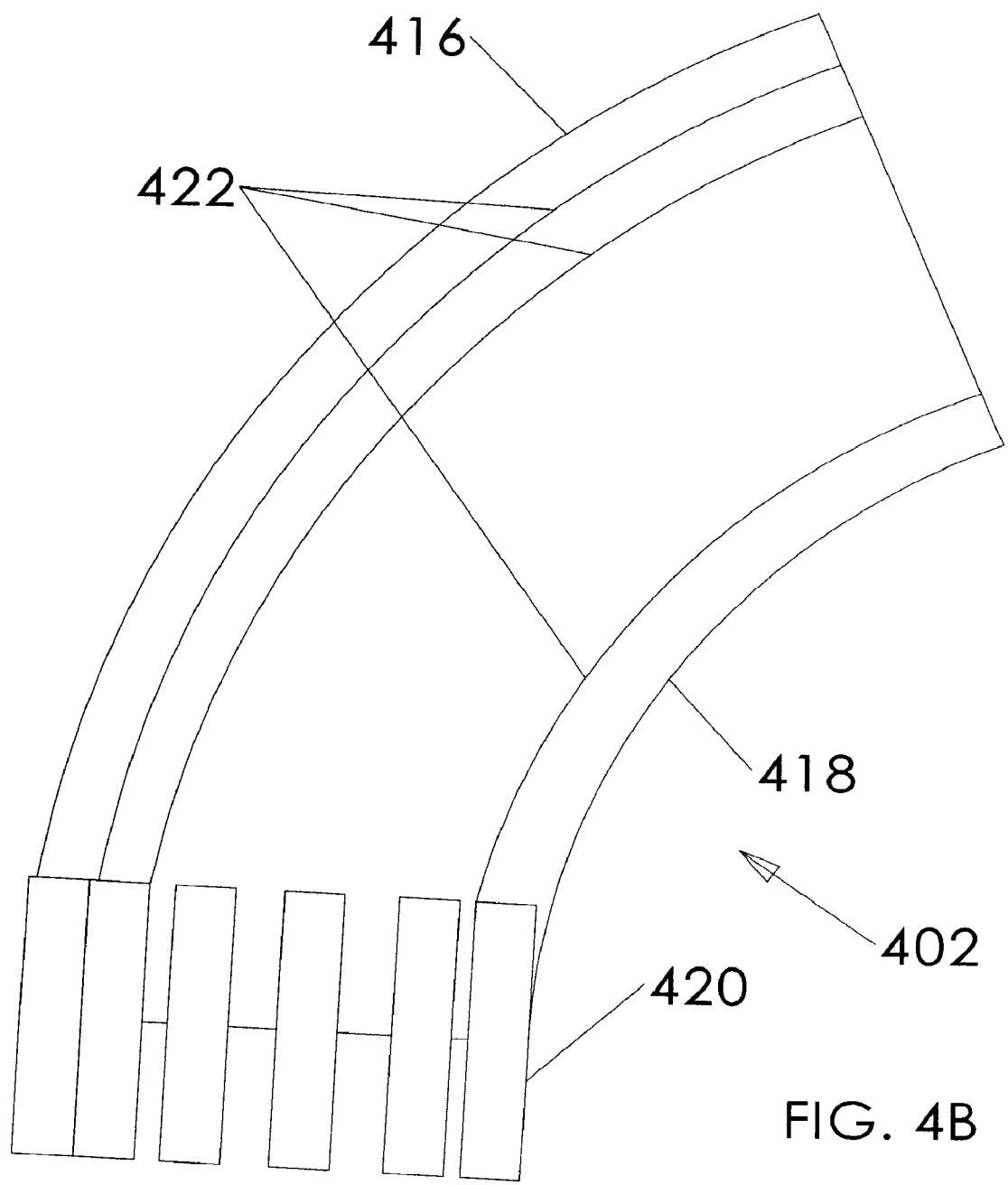
FIG. 4B illustrates an isometric view of a tear-to-size sleeve for an off-weighting device according to some embodiments of the present invention.

FIG. 4B illustrates a tear-to-size sleeve 402 for an off-weighting device according to some embodiments of the present invention. Straps 420 with hook-and-loop fasteners may be integral to sleeve 402; for example, straps 420 may be sewn onto sleeve 402. Reclosable fasteners 420, such as hook and loop tape, are used to secure sleeve 402 to itself after it is wrapped around the leg. Sleeve 402 may be shaped in an open-ended, downward-pointing conical shape, such that a circumference of upper edge 416 of sleeve 402 is larger than a circumference of lower edge 418 of sleeve 402. According to some embodiments of the present invention, the circumference of upper edge 416 is approximately 23.5 inches and the circumference of lower edge 418 is approximately 12.5 inches. Sleeve 402 may include perforations 422 to permit a user to reduce the circumference of upper edge 416 or increase the circumference of lower edge 418 by tearing at the perforations to customize sleeve 402 to the user's particular anatomy. According to some embodiments of the present invention, sleeve 402 comprises one or more bladders that may be filled with air or other conformable material which is then wrapped around the leg. This material may harden following application of sleeve 402 to the leg. For application to the calf area, sleeves 116, 400, 402 are preferably positioned up to or above the widest portion of the calf.

Figure 2:
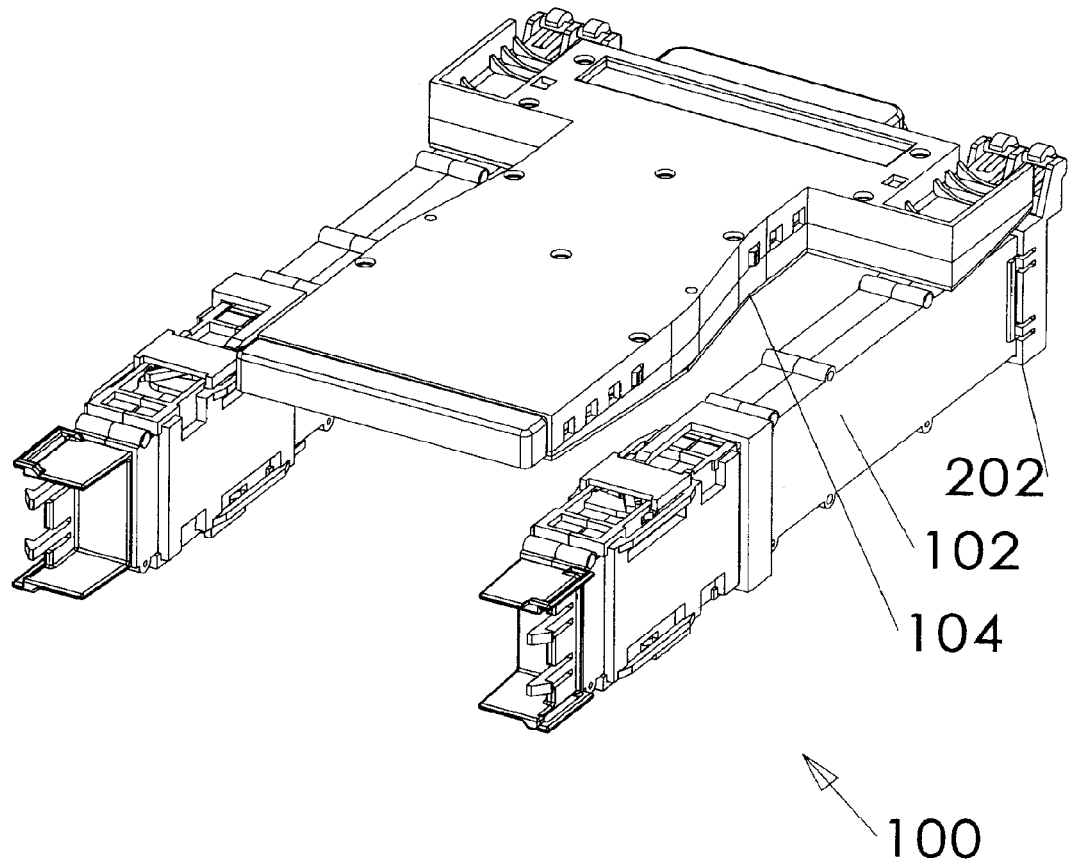
FIG. 2 illustrates an isometric view of an off-weighting device in a folded position according to some embodiments of the present invention.
Figure 5:
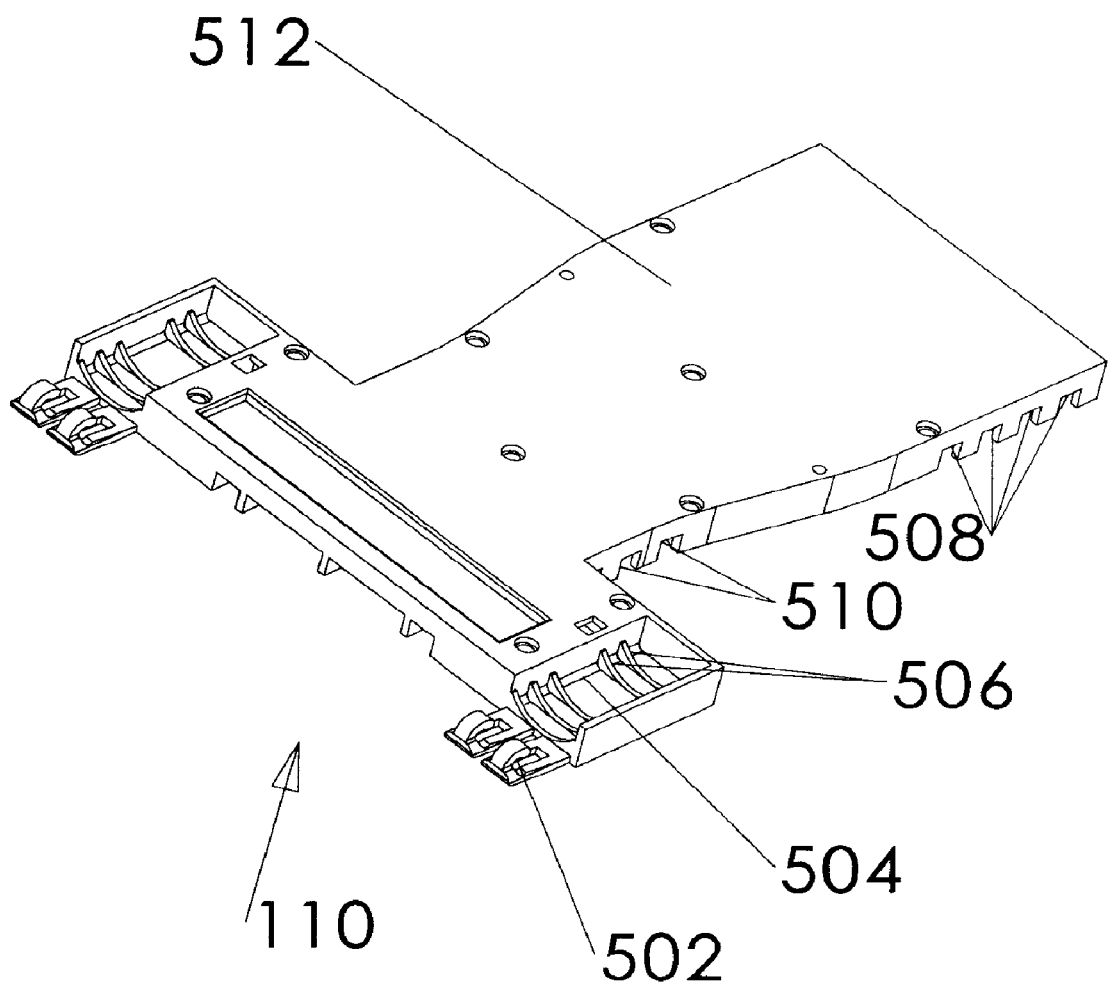
FIG. 5 illustrates an isometric view of a foot plate according to some embodiments of the present invention.
Figure 15A:
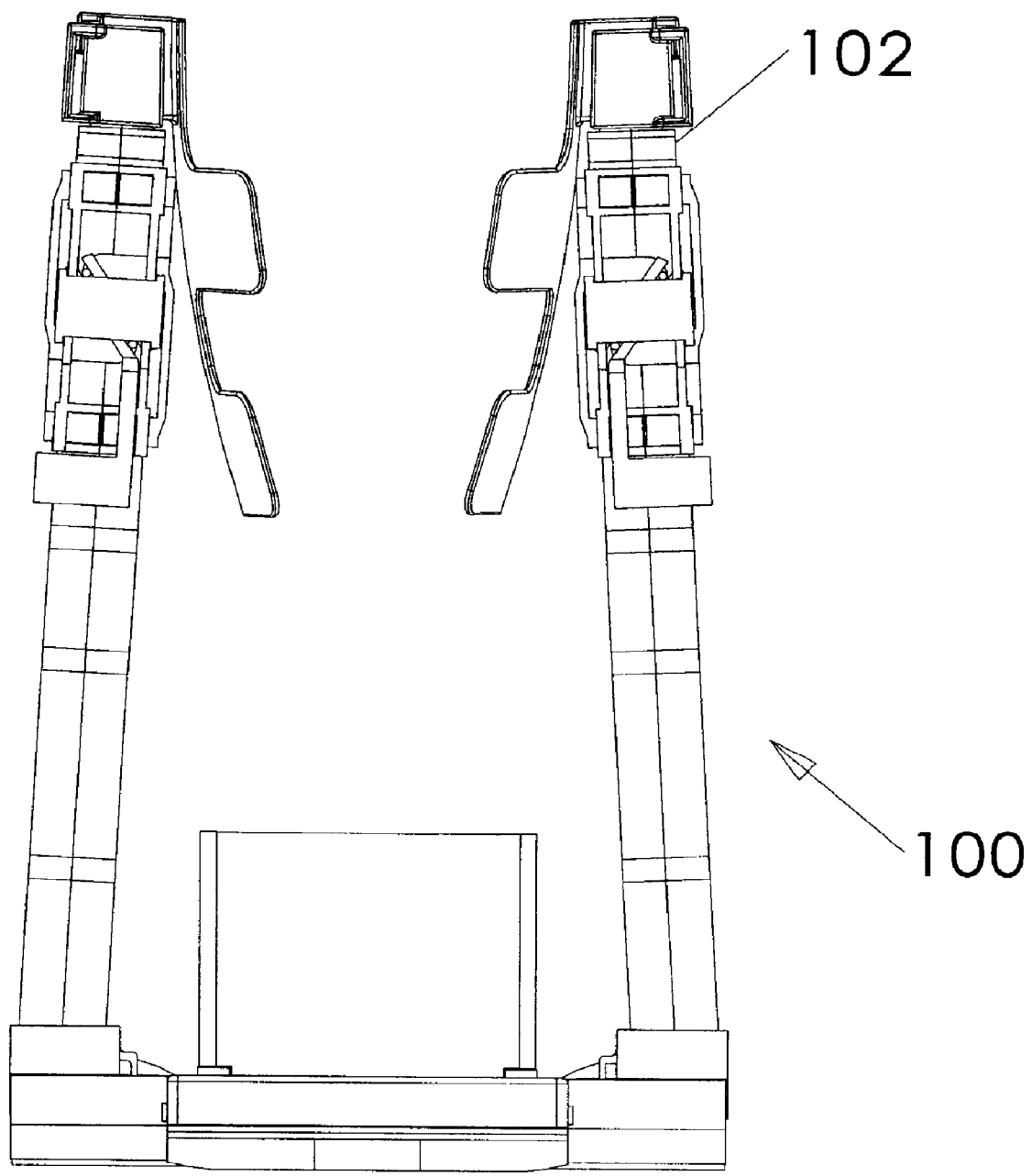
FIG. 15A illustrates a front perspective view of an off-weighting device showing support struts angled to fit a calf of minimum width according to some embodiments of the present invention.
Figure 15B:
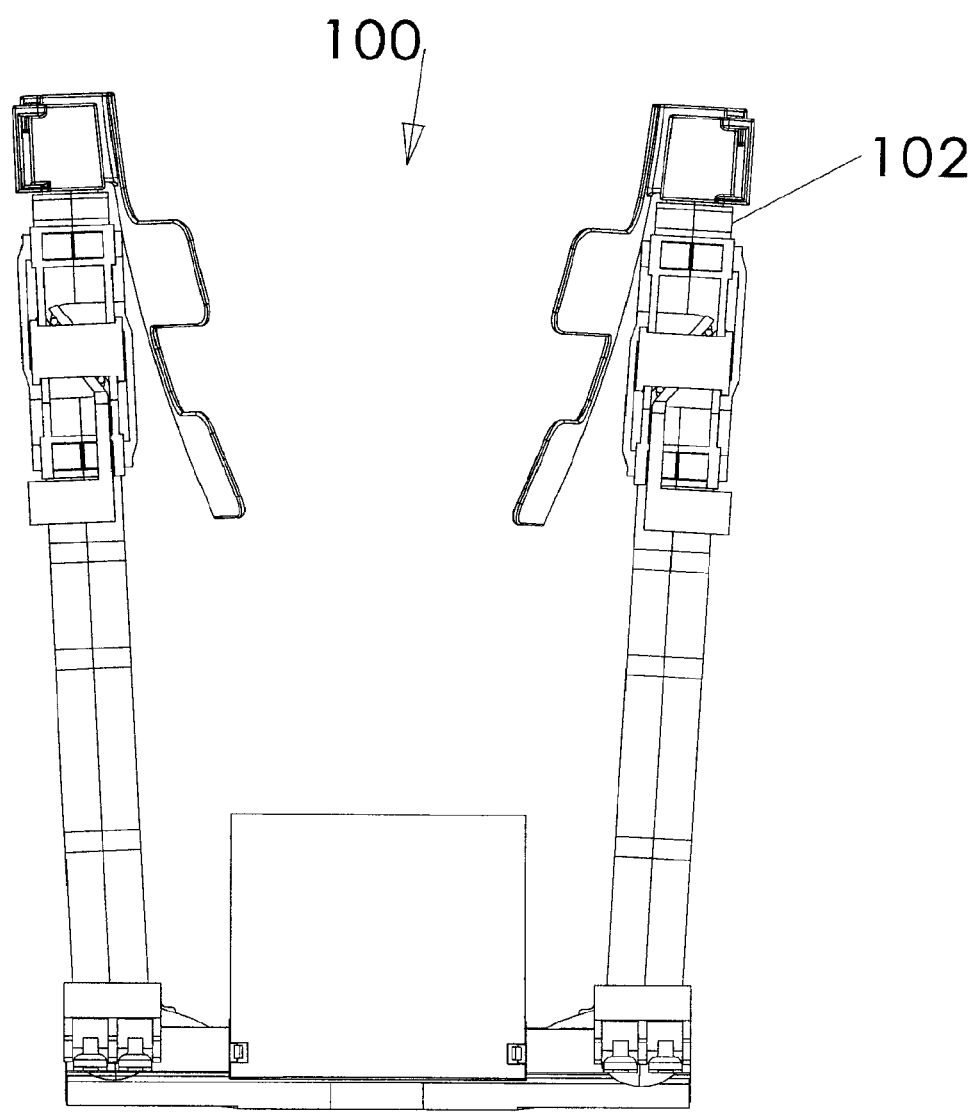
FIG. 15B illustrates a front perspective view of an off-weighting device showing support struts angled to fit a calf of maximum width according to some embodiments of the present invention.

Because off-weighting device 100 may be packaged in a folded or collapsed configuration, as depicted in FIG. 2, the user may need to rotate foot assembly 104 around strut pivot 202 until off-weighting device 100 is in the assembled position of FIG. 1. FIG. 5 illustrates an isometric view of a foot plate 110 according to some embodiments of the present invention, illustrating strut pivot attachment clips 502. Strut pivot attachment clips 502 may be configured to clip onto and/or interface with pins on strut pivot 202. Once foot assembly 104 and/or foot plate 110 have been rotated to the assembled position of FIG. 1, the ends of support struts 102 sit within strut pockets 504 formed within foot plate 110. Semi-circular support areas 506 within strut pocket 504 may serve to allow struts 102 to tilt in and out to adjust for various calf widths, as illustrated in the discussion of FIGS. 15A and 15B, below. The bottom of outer strut 118 may be rounded to allow outer strut 118 to rest in strut pocket 504 and to pivot on semi-circular support areas 506 to maintain maximum contact with foot plate 110. Slots 508 in the sides of foot plate 110 receive the release tabs of toe extender 106, and slots 510 in the sides of foot plate 110 receive the release tabs of heel extender 302. Hook tape may be affixed to a top surface 512 of foot plate 110 to secure a foot pad to foot plate 110. The dimensions of strut pocket 504 area of foot plate 110 may at least partially define the ability of off-weighting device 100 to adjust to different patients through the tilting in and out of support struts 102. A bottom surface of foot plate 110 may include ribbing, such as a criss-cross pattern of ribbing, in order to increase the stiffness of foot plate 110.

Figure 6:
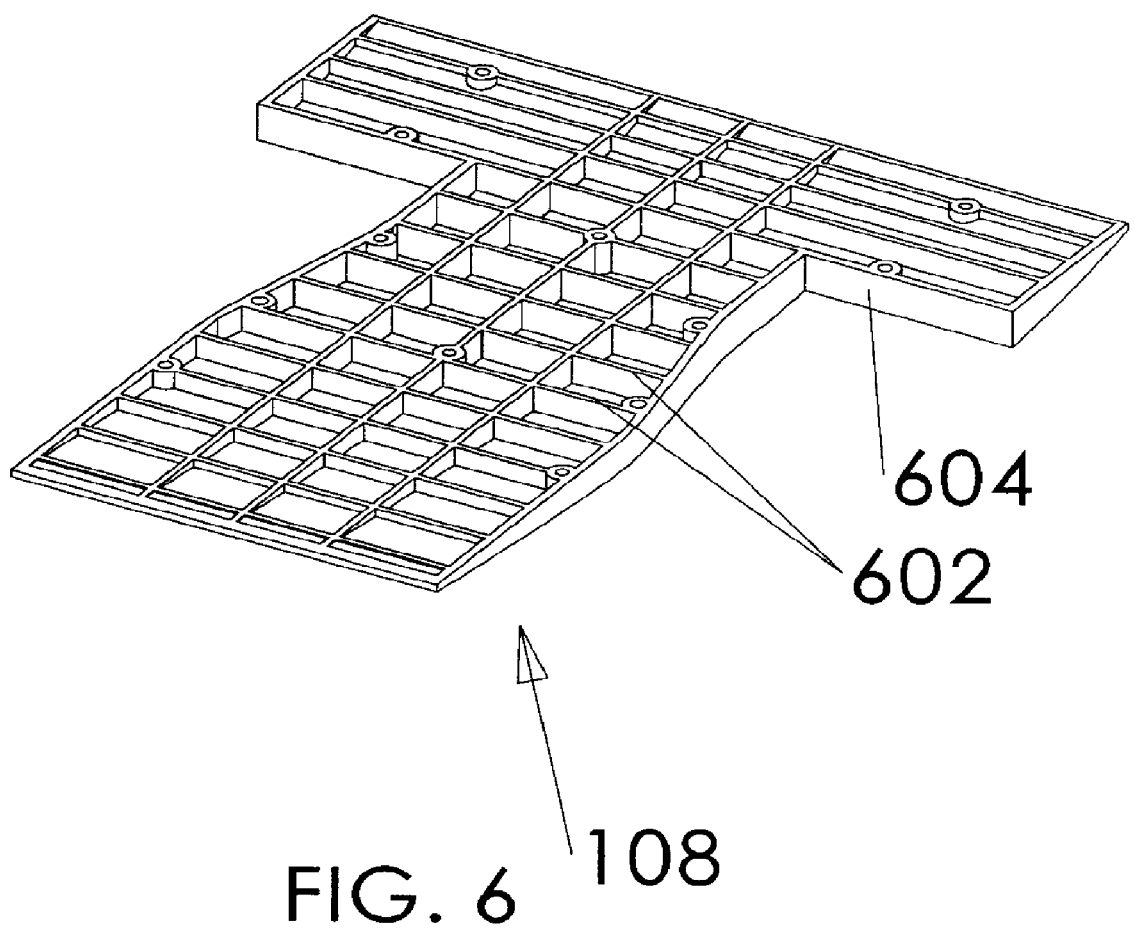
FIG. 6 illustrates an isometric view of a stiffener according to some embodiments of the present invention.

FIG. 6 illustrates an isometric view of a top surface of stiffener 108 according to some embodiments of the present invention. Stiffener 108 may be affixed directly under foot plate 110. In a fashion similar to that found on a bottom surface of foot plate 110, stiffener 108 may include ribbing 602, such as criss-cross ribbing, to further add strength to foot plate 110 and minimize the flexing of foot assembly 104 between support struts 102. Stiffener 108 is also operable to transfer load between the ground and foot plate 110. The bottom surface of stiffener 110 may be curved to provide a rocker sole to foot assembly 104. The thickest part 604 of such a rocker may be located to align with the forward edge of struts 102. Because the bottom surface of stiffener 108 is configured to interface with the ground or other underlying surface, a tread 304 may be affixed to the bottom surface of stiffener 108. Tread 304 may improve the traction of foot assembly 104 and thus off-weighting device 100 and may provide minimal cushioning during ambulation. A complicated tread design may not be desired for short-term use embodiments of the present invention. Tread 304 may be die-cut from a sheet of prefabricated tread material and may have pressure-sensitive adhesive applied. Alternatively, tread 304 may be over-molded onto foot assembly 104. The joining of footplate 110 to stiffener 108 through a means such as screws or welding may create the pockets into which toe extender 106 and heel extender 302 slide.

Figure 7A:
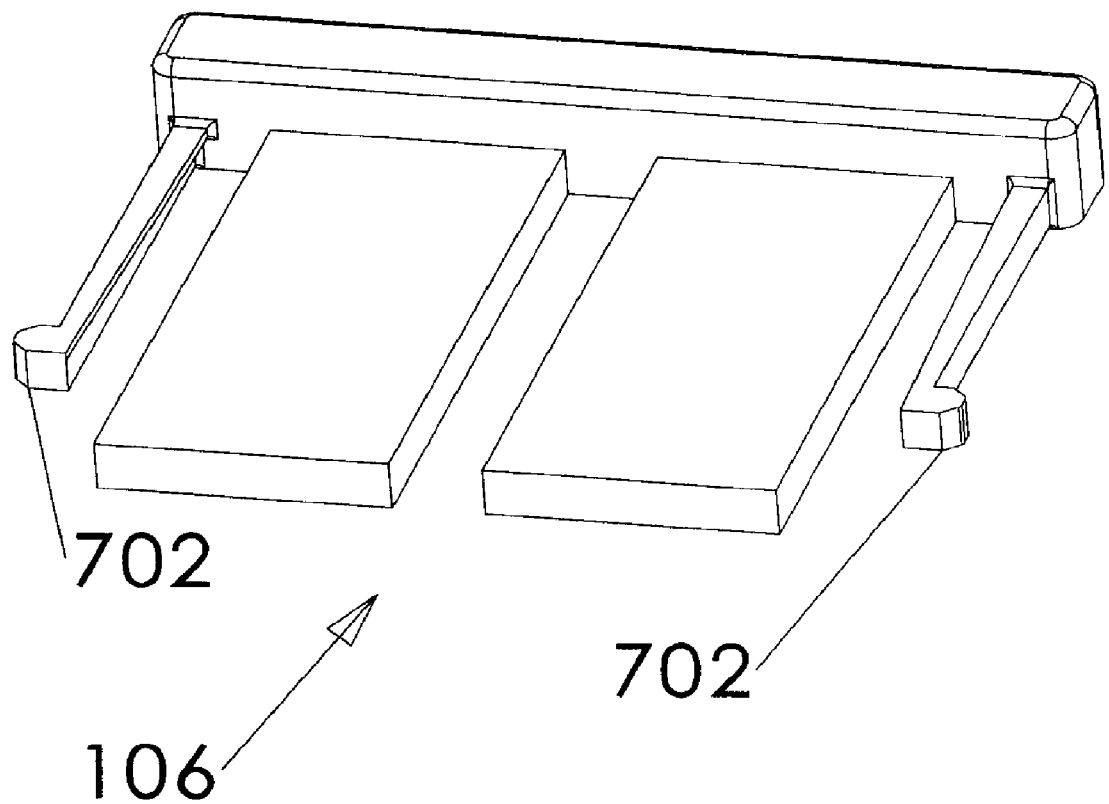
FIG. 7A illustrates an isometric view of a toe extender according to some embodiments of the present invention.
Figure 7B:
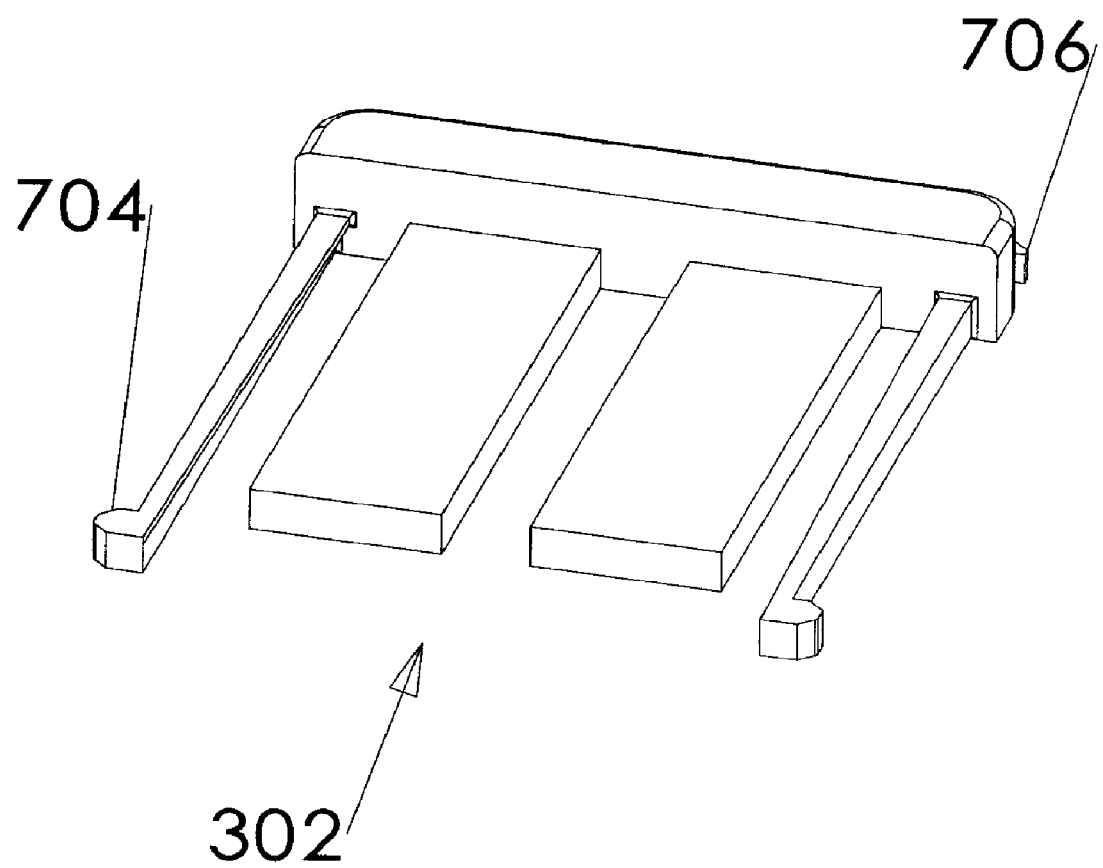
FIG. 7B illustrates an isometric view of a heel extender according to some embodiments of the present invention.

FIG. 7A illustrates an isometric view of a toe extender 106 according to some embodiments of the present invention. Toe extender 106 may include release tabs 702; toe extender 106 may be inserted into the front of foot assembly 104 as depicted in FIG. 3, such that release tabs 702 interface and/or lock within slots 508. FIG. 7B illustrates an isometric view of a heel extender 302 according to some embodiments of the present invention. Heel extender 302 may include release tabs 704 and heel support locking tabs 706. Heel extender 302 may be inserted into the back of foot assembly 104 as depicted in FIG. 3, such that release tabs 704 interface and/or lock within slots 510. In addition, heel support 112 may be coupled to heel extender 302 via heel support locking tabs 706, which may help to hold heel support 112 in place.

The lengths at which toe extender 106 and/or heel extender 302 protrude from foot assembly 104 may be adjusted by pushing release tabs 702 and/or 704 to disengage the release tabs 702 and/or 704 from foot assembly 104 and by sliding toe extender 106 and/or heel extender 302 in or out of foot assembly 104 until release tabs 702 and/or 704 engage a separate set of slots 508 and/or 510. In this way, toe extender 106 and/or heel extender 302 may be adjusted to accommodate different foot sizes. According to some embodiments of the present invention, slots 508, 510 are separated by increments of one half inch, for a total adjustment of an additional one and a half inches to the toe end and one inch to the heel end. Toe extender 106 and/or heel extender 302 may also serve to protect the user's foot from a bumping the heel or toe against a hard surface.

Figure 7C:
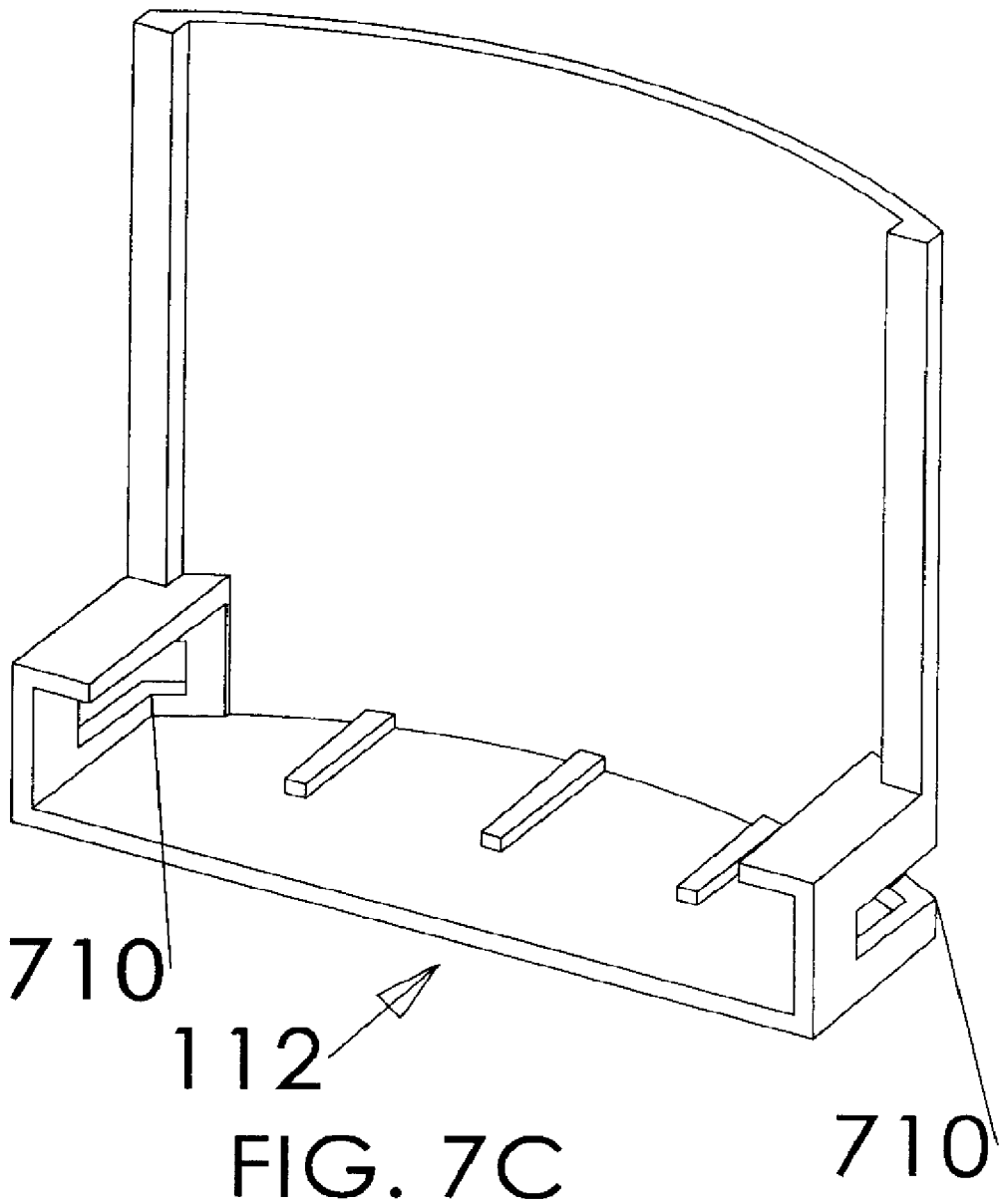
FIG. 7C illustrates an isometric view of a heel support according to some embodiments of the present invention.

FIG. 7C illustrates an isometric view of heel support 112 according to some embodiments of the present invention. Heel support foam (not shown) made from a piece of one-half inch 4.35 pound Lindell HSSX7 material may be affixed to heel support 112 with a pressure sensitive adhesive. Slots 710 of heel support 112 may snap onto heel support locking tabs 706 of heel extender 302. Heel support 112 may prevent motion of the user's heel relative to the rest of off-weighting device 100. Off-weighting device 100 may be shipped without heel support 112 installed, after which the user may snap heel support 112 into heel extender 302 if needed. According to some embodiments of the present invention, heel support 112 employs a strap threaded through heel support 112 to hold the user's heel to heel support 112. According to other embodiments, a padded heel support 112 may be utilized without a strap.

Figure 8:
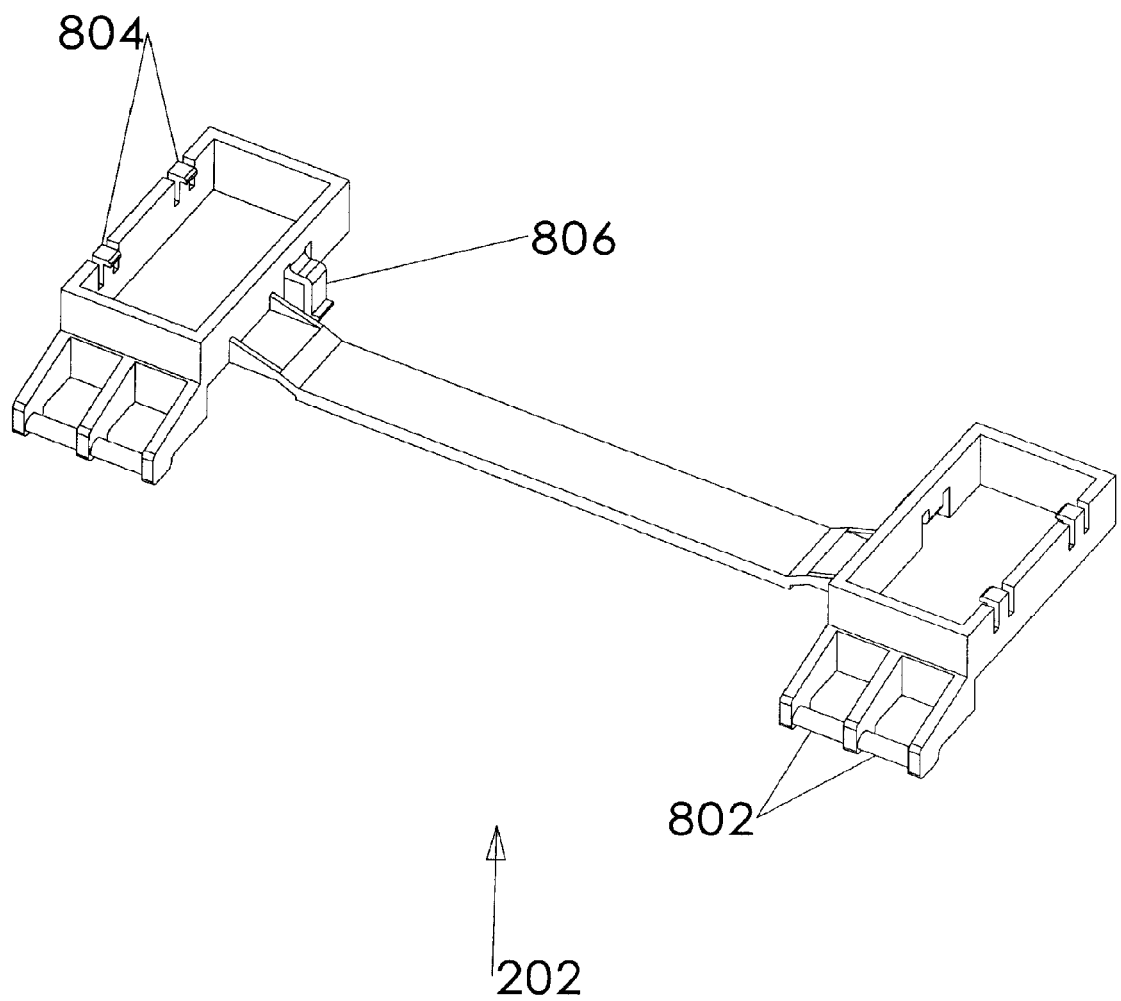
FIG. 8 illustrates an isometric view of a strut pivot according to some embodiments of the present invention.

FIG. 8 illustrates an isometric view of strut pivot 202 according to some embodiments of the present invention. Strut pivot 202 may serve several functions. First, strut pivot 202 may hold support struts 102 during storage and may allow both struts 102 to be rotated into an assembled position at the same time. A pin 802 on strut pivot 202 that snaps into foot plate 110 may be flattened on one side, such that when strut pivot 202 is rotated until the flattened side of pin 802 is aligned with the opening formed by strut pivot attachment clips 502, strut pivot 202 may be easily assembled to foot plate 110. However, when strut pivot 202 is rotated into the assembled position for use, the interference between pins 802 and strut pivot attachment clips 502 is larger and thus prevents disassembly of foot plate 110 from strut pivot 202. Strut pivot may be coupled to support struts 102 via snap hooks 804, and snap hooks 806 may secure strut pivot 202 to foot plate 110 when foot assembly 104 has been rotated into an assembled position.

Figure 9A:
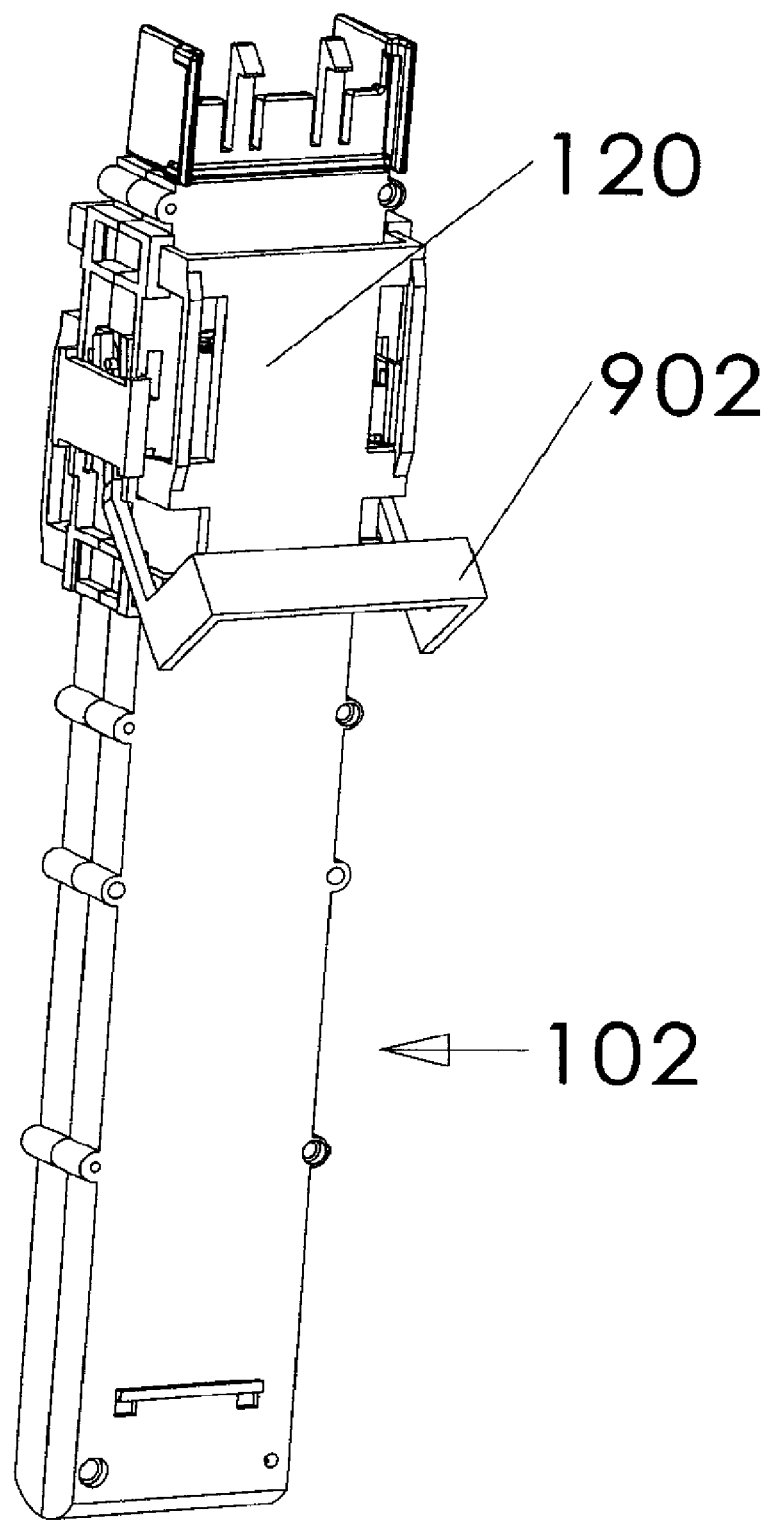
FIG. 9A illustrates an isometric view of a support strut with a strut latch in an open position according to some embodiments of the present invention.
Figure 9B:
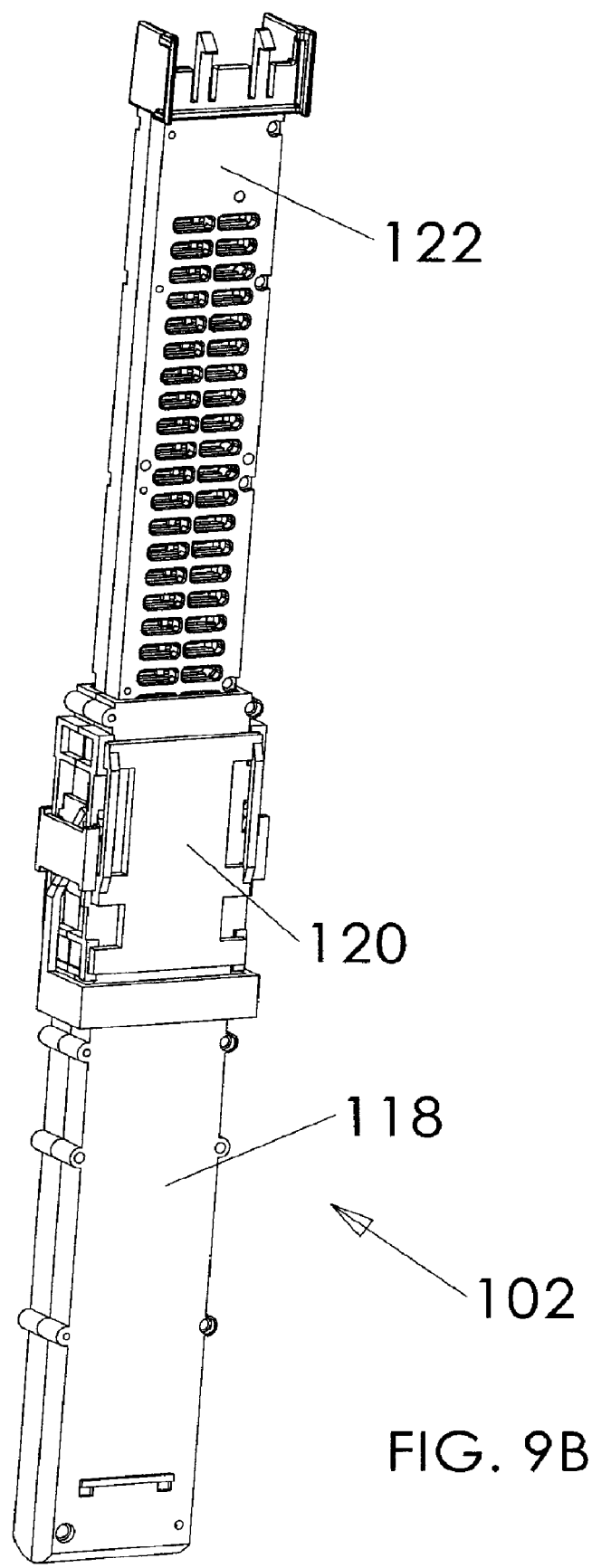
FIG. 9B illustrates an isometric view of an extended support strut with a strut latch in a closed position according to some embodiments of the present invention.

According to some embodiments of the present invention, support struts 102 include inner strut 122 and outer strut 118. FIG. 9A illustrates an isometric view of such a support strut 102 with a strut latch 120 in an open position according to some embodiments of the present invention. A latch lever 902 may be used to open or close strut latch 120; for example, latch lever 902 may rest against support strut 102 in a closed position and may be lifted away from support strut 102 to open strut latch 120 as depicted in FIG. 9A. FIG. 9B illustrates an isometric view of an extended support strut 102 with a strut latch 120 in a closed position according to some embodiments of the present invention.

Figure 9C:
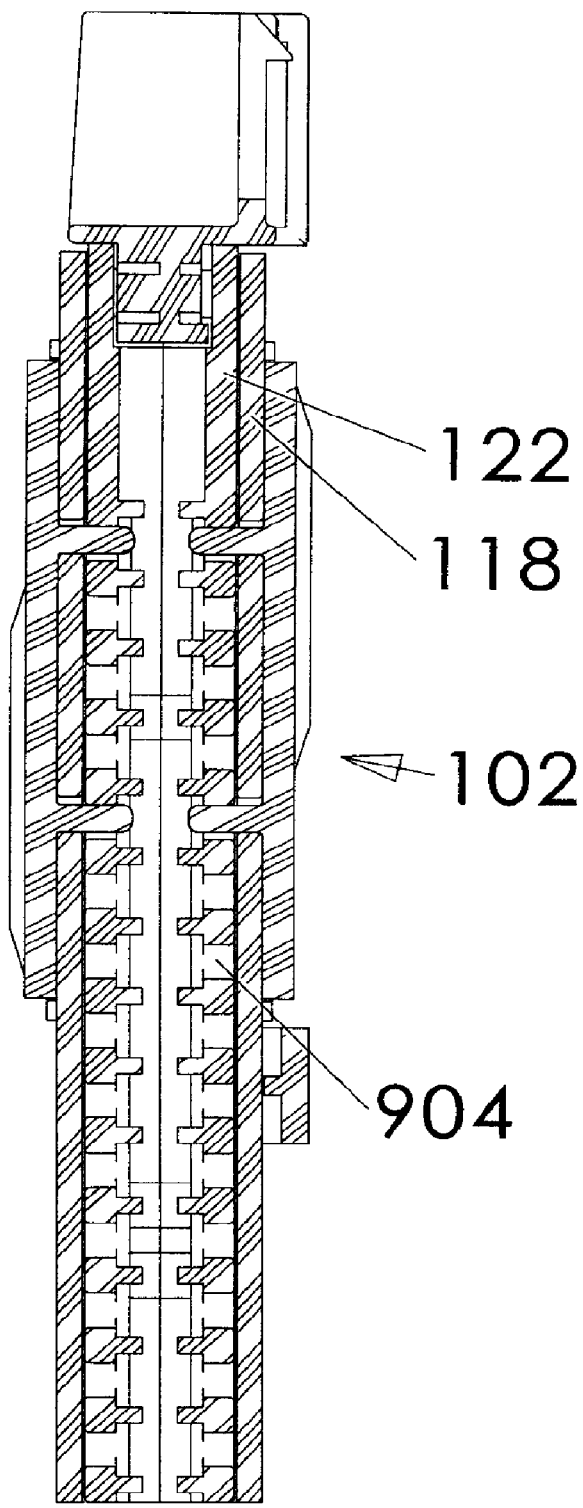
FIG. 9C illustrates a partial side cross-sectional view of a support strut with a strut latch in a closed position according to some embodiments of the present invention.
Figure 9D:
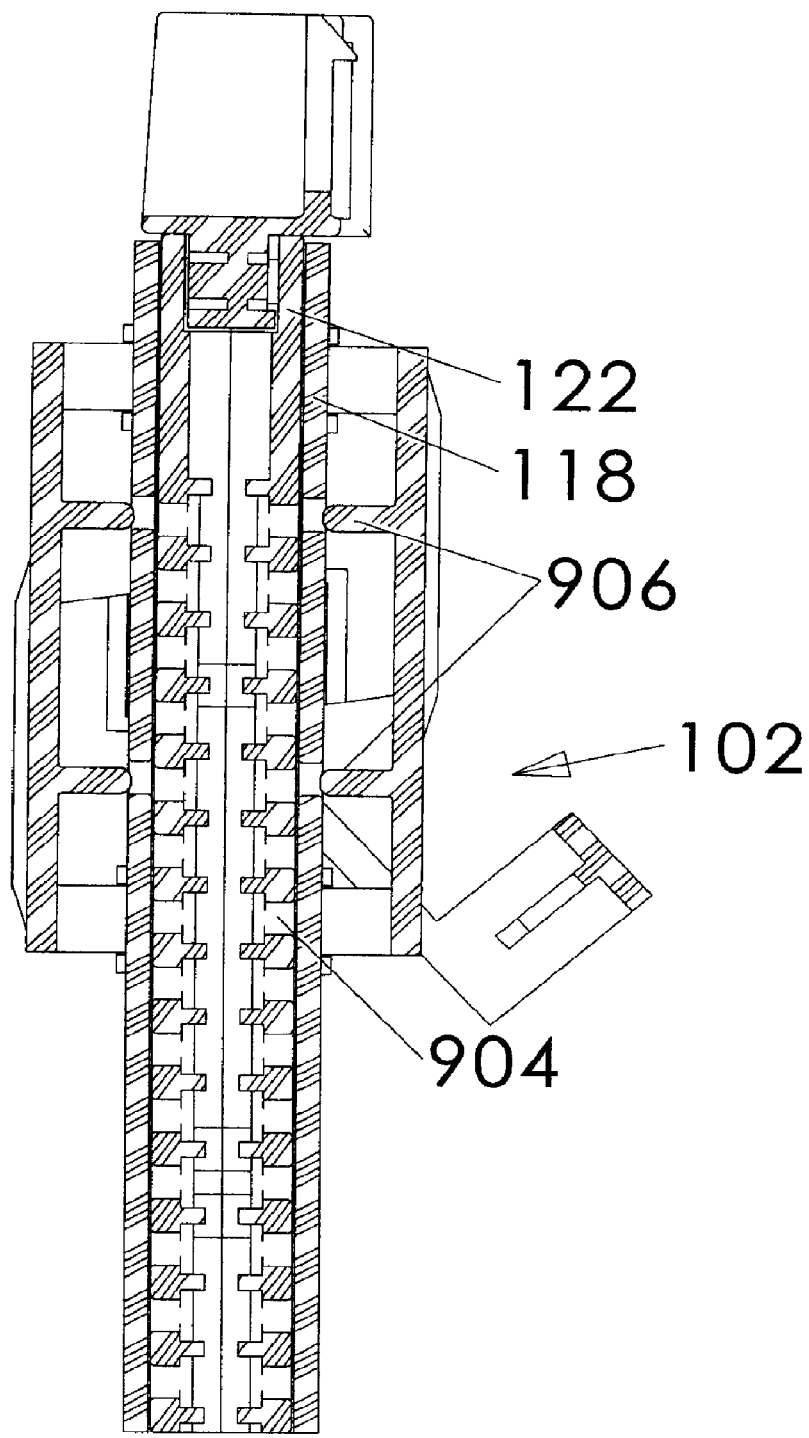
FIG. 9D illustrates a side cross-sectional view of a support strut with a strut latch in an open position according to some embodiments of the present invention.
Figure 10:
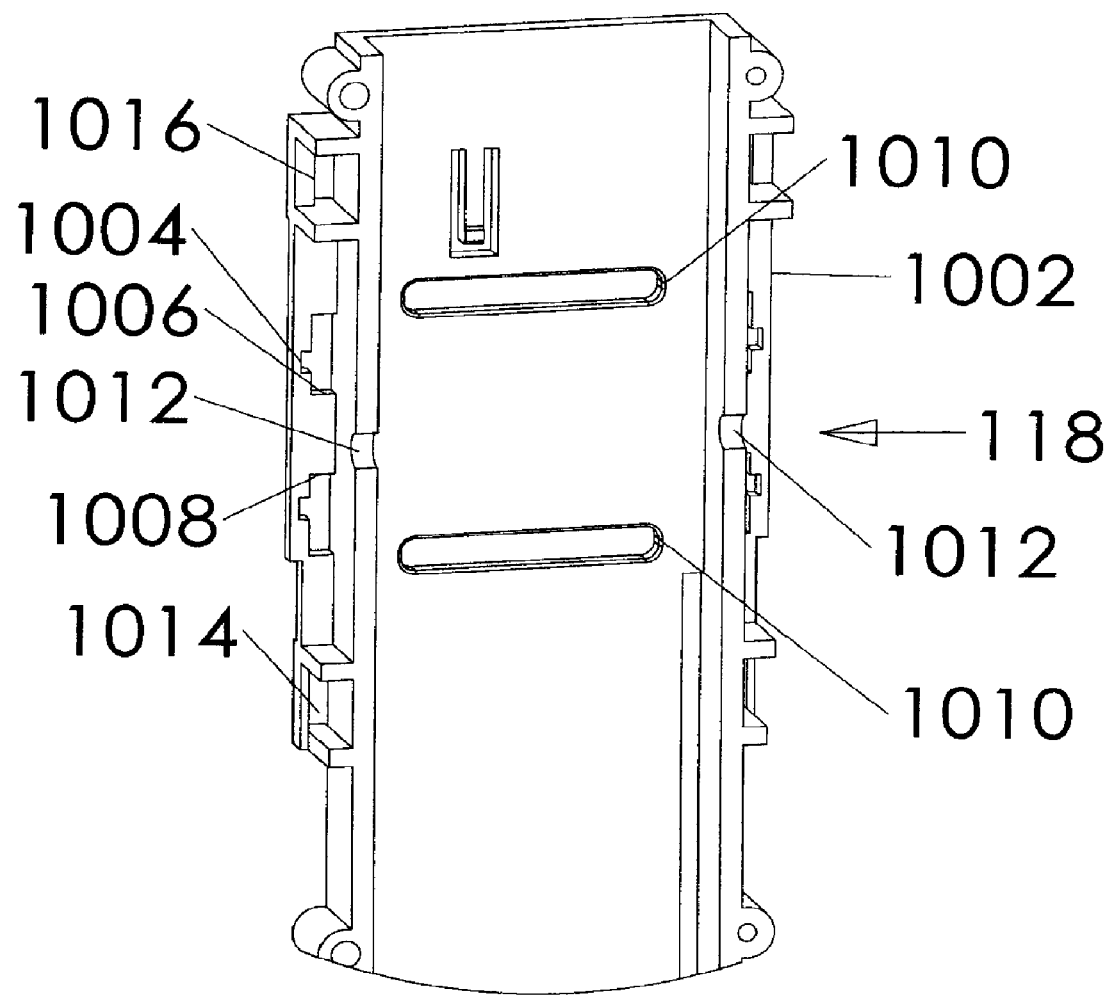
FIG. 10 illustrates an isometric view of an end of a support strut showing a side rib structure according to some embodiments of the present invention.

Referring now to FIGS. 9C, 9D, and 10, FIG. 9C illustrates a partial side cross-sectional view of support strut 102 with strut latch 120 in a closed position, and FIG. 9D illustrates a side cross-sectional view of support strut 102 with strut latch 120 in an open position, according to some embodiments of the present invention. Inner strut 122 may include a series of ribs 904, and outer strut 118 may include slots 1010, as depicted in FIG. 10, to allow teeth 906 of strut latch 120 to pass through outer strut 118 to interlock with ribs 904 on inner strut 122 when strut latch 120 is in a closed position.

Figure 11:
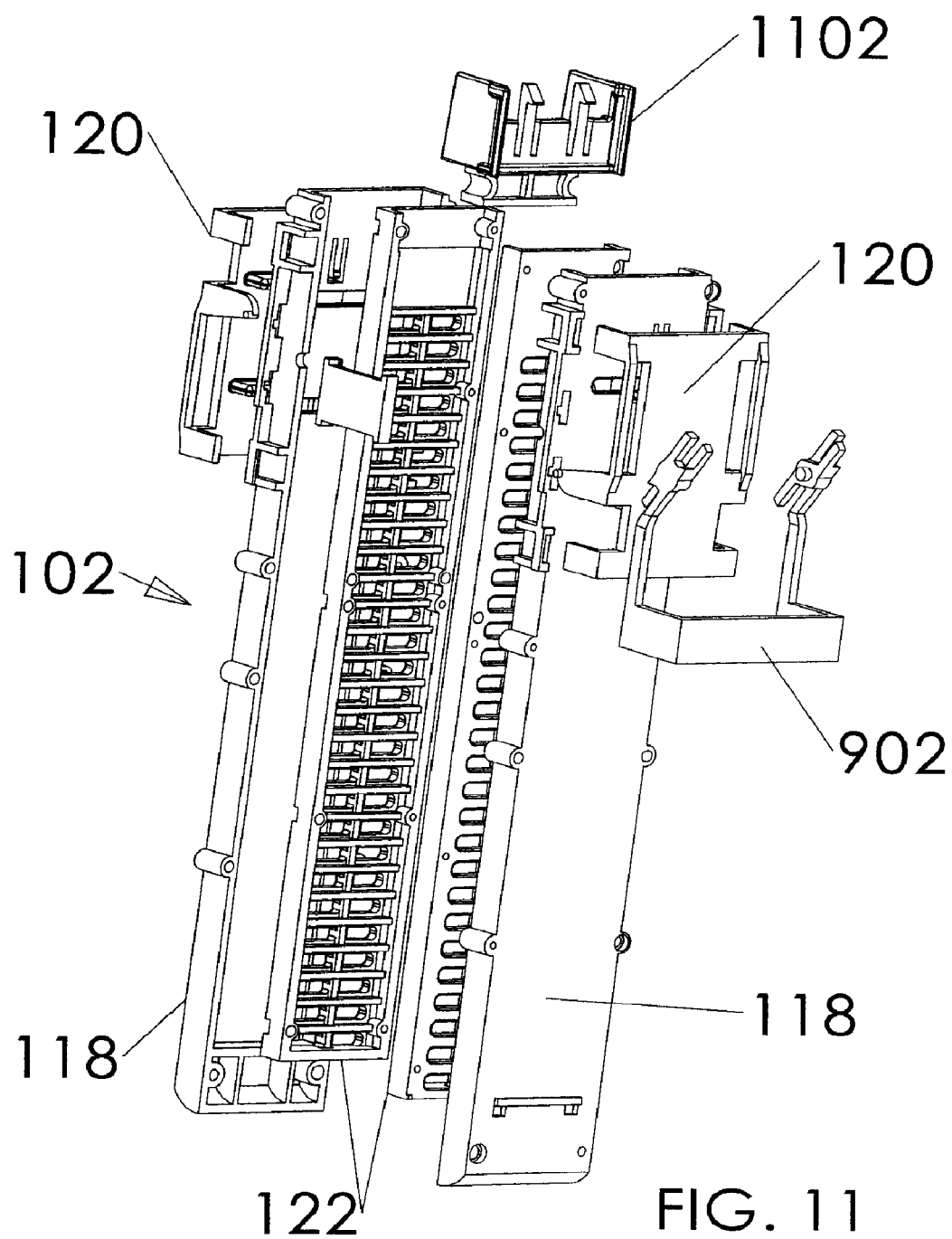
FIG. 11 illustrates an exploded isometric view of a support strut according to some embodiments of the present invention.
Figure 12A:
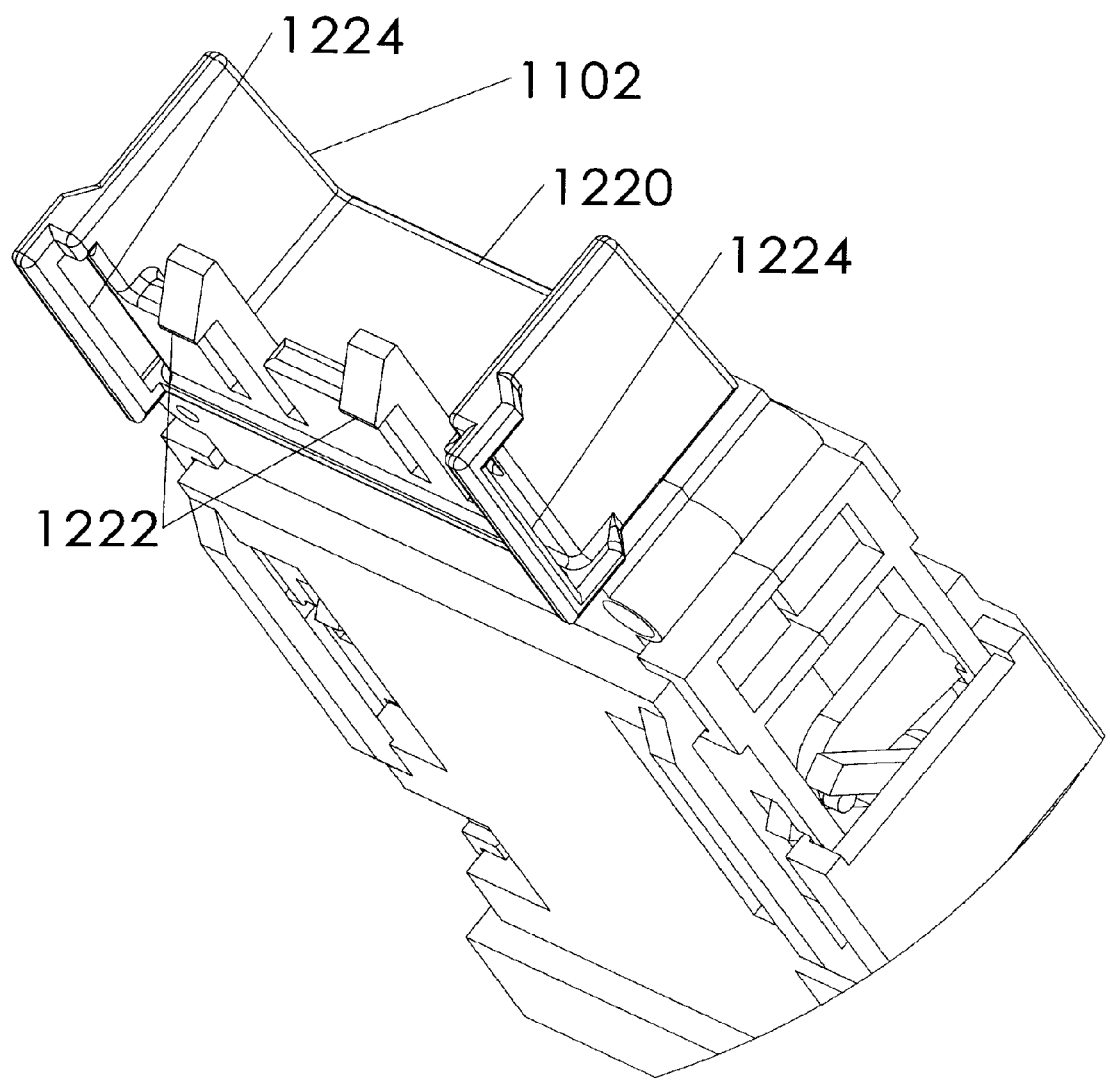
FIG. 12A illustrates a partial isometric view of a top of an inner strut according to some embodiments of the present invention.
Figure 12B:
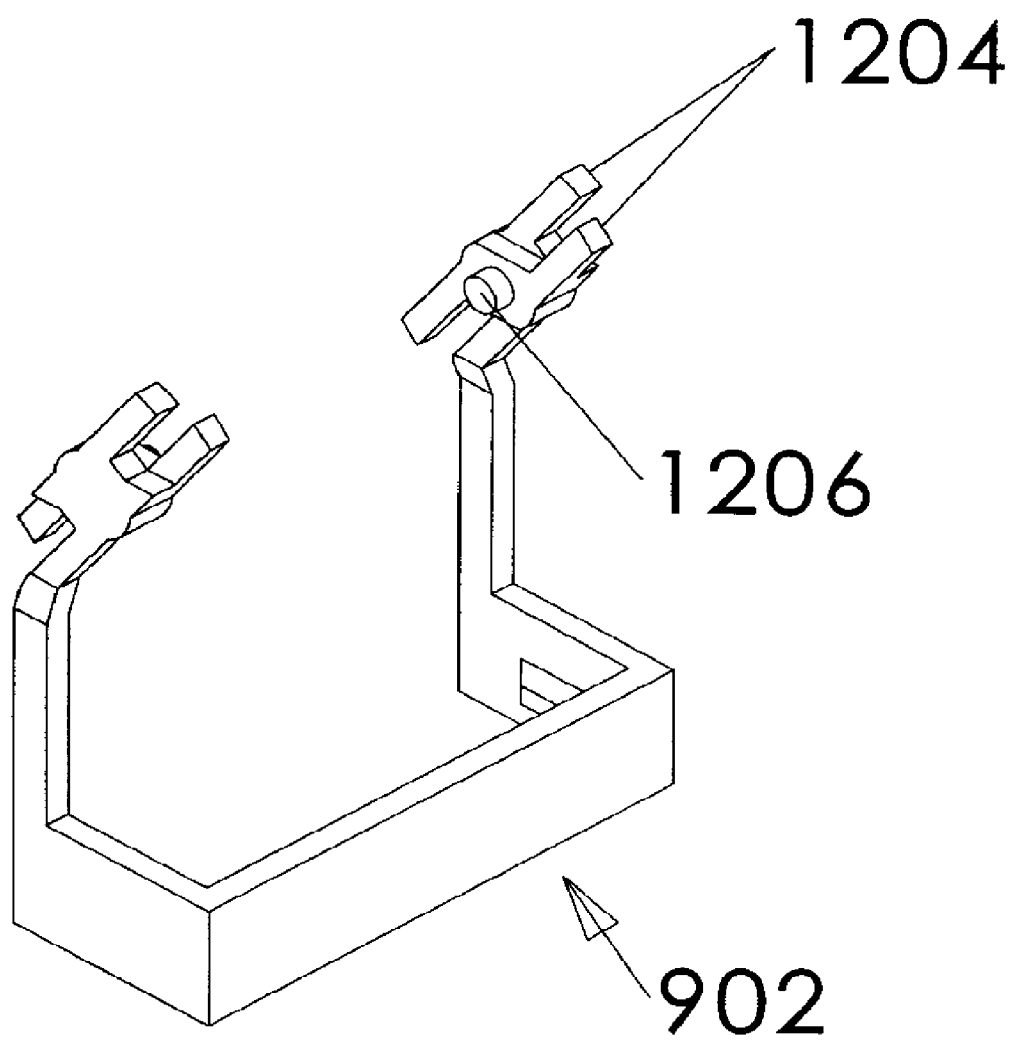
FIG. 12B illustrates an isometric view of a latch lever according to some embodiments of the present invention.
Figure 12C:
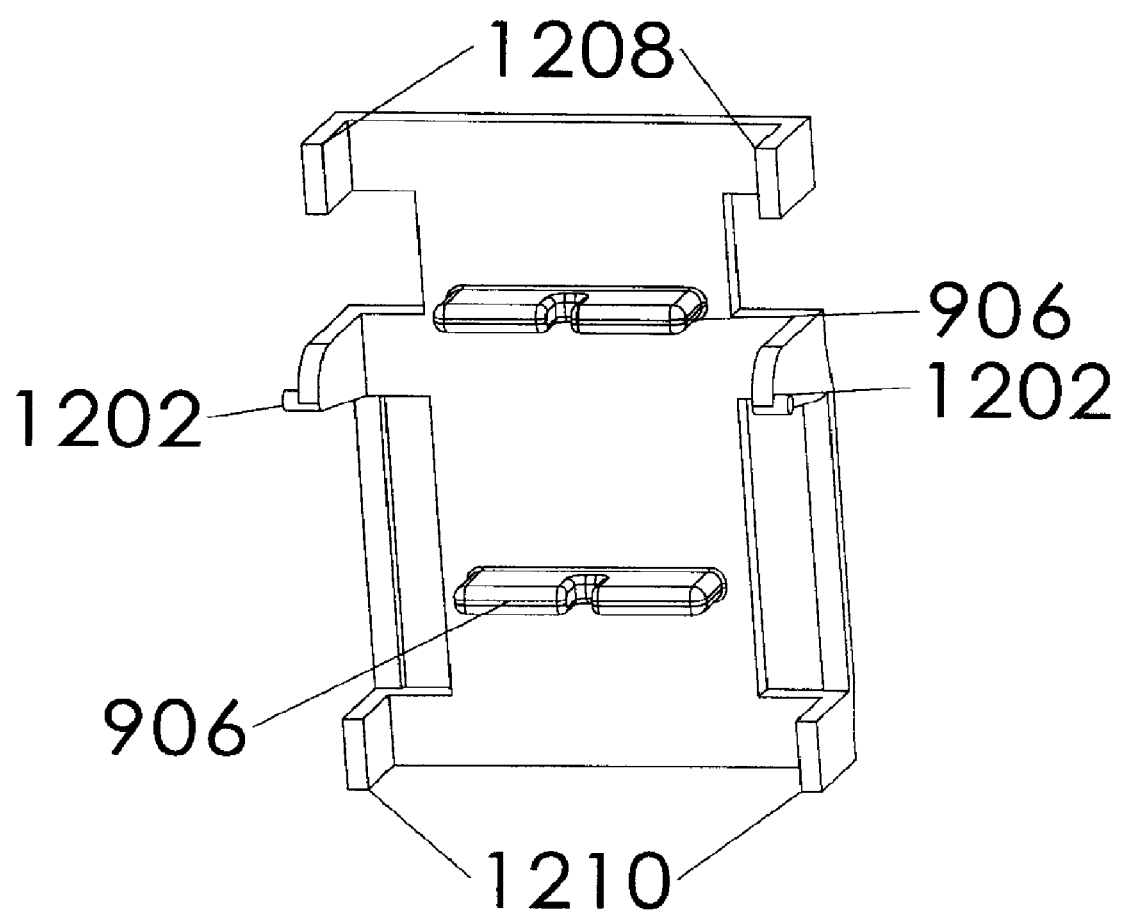
FIG. 12C illustrates an isometric view of a strut latch according to some embodiments of the present invention.

Referring now to FIGS. 10, 11, and 12B-12C, FIG. 10 illustrates an isometric view of one half of an end of outer strut 118 showing a side rib structure 1002 according to some embodiments of the present invention. FIG. 11 illustrates an exploded isometric view of support strut 102 according to some embodiments of the present invention. FIG. 12B illustrates an isometric view of latch lever 902, and FIG. 12C illustrates an isometric view of strut latch 120, according to some embodiments of the present invention. Latch lever 902 may include pivot pins 1206 and forked arms 1204. Strut latch 120 may include protrusions 1208, protrusions 1210, and lever interface pins 1202.

When each of the halves of outer strut 118 are assembled, such as, for example, by being welded together with a tongue-and-groove weld or held together via screws or other fasteners, holes 1012 are formed on each side of outer strut 118. Pivot pins 1206 of latch lever 902 are configured to be inserted within holes 1012, such that rotating latch lever 902 causes forked arms 1204 to rotate in the same direction. Outer strut 118 may include side rib structure 1002; side rib structure 1002 has formed therein protrusion holes 1016, protrusion holes 1014, and stops 1006, 1008 for forked arms 1204. Stops 1006, 1008 operate to limit movement of latch lever 902. For example, when latch lever 902 rests in a closed position against outer strut 118, forked arm 1204 may rest against stop 1006; and when latch lever 902 is rotated away from outer strut 118, forked arm 1204 may rest against stop 1008. The size and configuration of stops 1006, 1008 may determine the range of rotation of latch lever 902. A slight chamfer 1004 may be formed near each stop 1006, 1008 to create a minor interference with forked arms 1204 as latch lever 902 is rotated into an open position, to minimize the chance that latch lever 902 releases and rotates back to a closed position as the user is attempting to open strut latch 120.

Protrusions 1208 of strut latch 120 are inserted into protrusion holes 1016 of outer strut 118; and protrusions 1210 of strut latch 120 are inserted into protrusion holes 1014 of outer strut 118. Lever interface pins 1202 on strut latch 120 are configured to extend between forked arms 1204 of latch lever 902, such that a rotation of latch lever 902 away from outer strut 118 causes a substantially linear movement of strut latch 120 away from outer strut 118. This, in turn, causes a retraction of teeth 906 from holes 1012, thereby disengaging teeth 906 from ribs 904 and permitting inner strut 122 to slide within outer strut 118. The length of support struts 102 may then be adjusted to the proper length by sliding inner strut 122 within outer strut 118. Once a proper length has been achieved, latch lever 902 may be rotated back towards outer strut 118 to a closed position, causing teeth 906 to protrude through holes 1010, thereby engaging teeth 906 with ribs 904 to once again prohibit movement of inner strut 122 with respect to outer strut 118.

FIG. 12A illustrates a partial isometric view of a top 1102 of inner strut 122 according to some embodiments of the present invention. Top 1102 may include a sleeve attachment pocket 1220, snap hooks 1222 for interfacing with sleeve attachment 114, and strap slots 1224. Sleeve attachments 114 are discussed further with respect to FIGS. 14A and 14B, below.

Figure 13A:
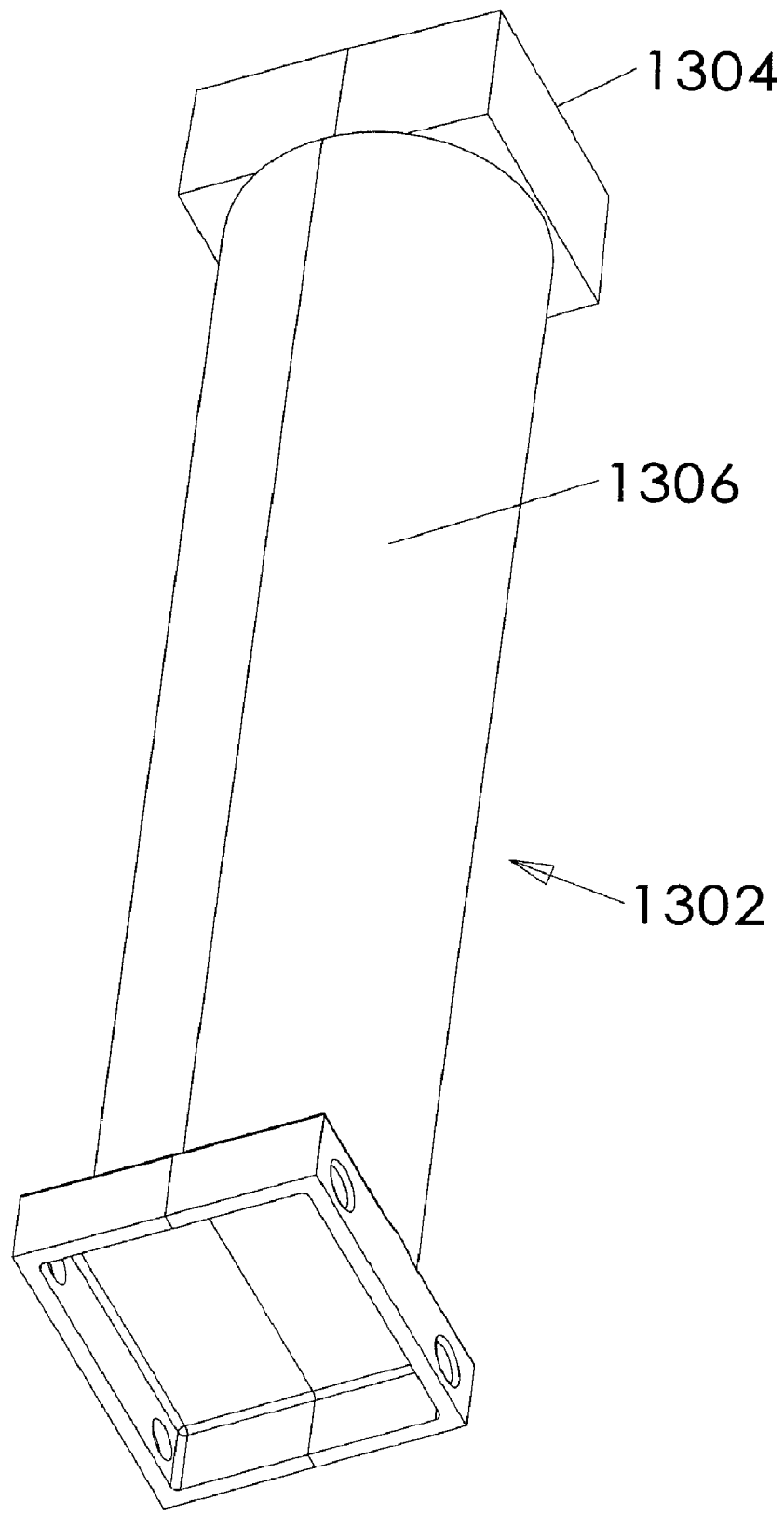
FIG. 13A illustrates an isometric view of an alternative support strut according to some embodiments of the present invention.
Figure 13B:
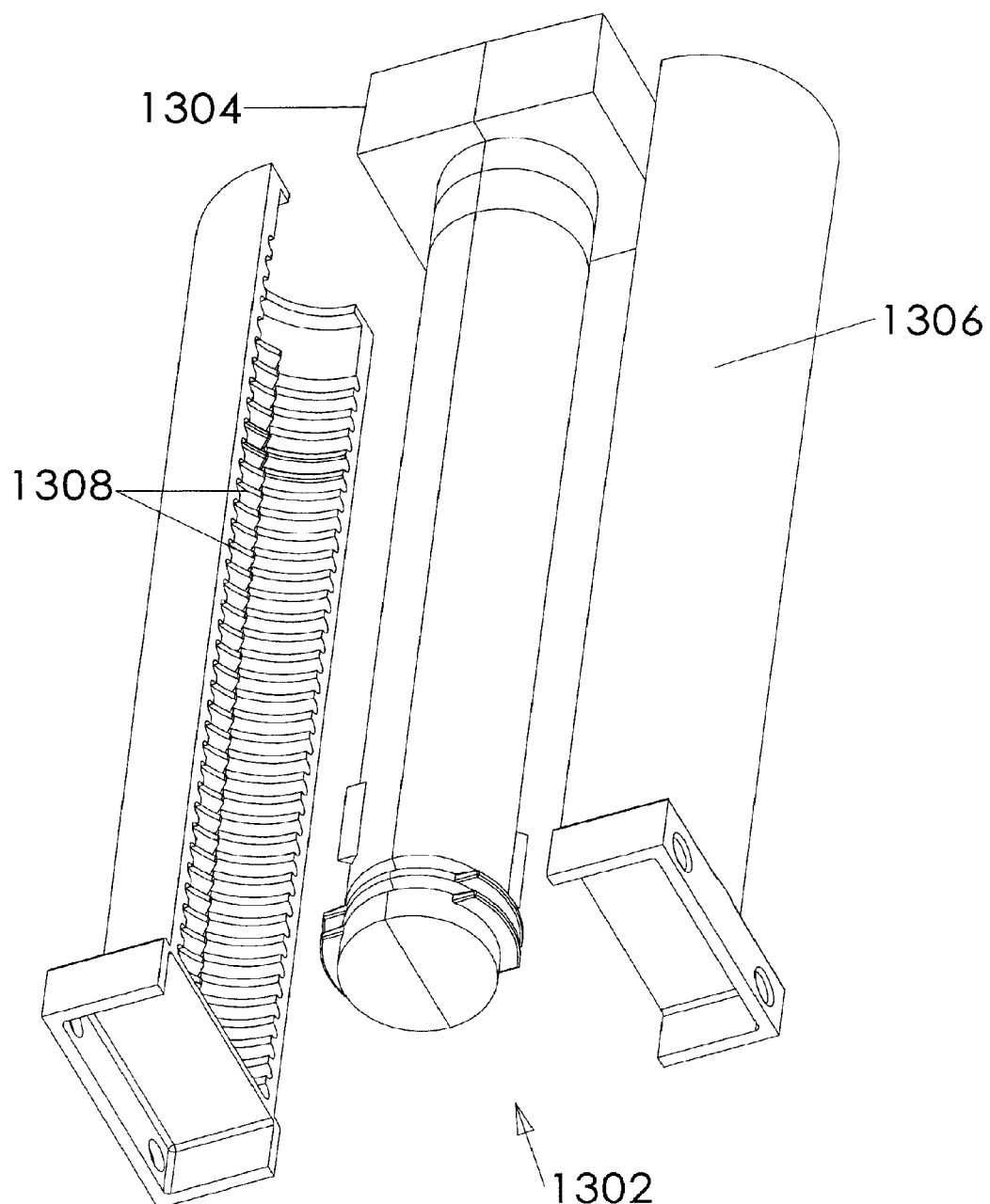
FIG. 13B illustrates an exploded isometric view of an alternative support strut according to some embodiments of the present invention.
Figure 13C:
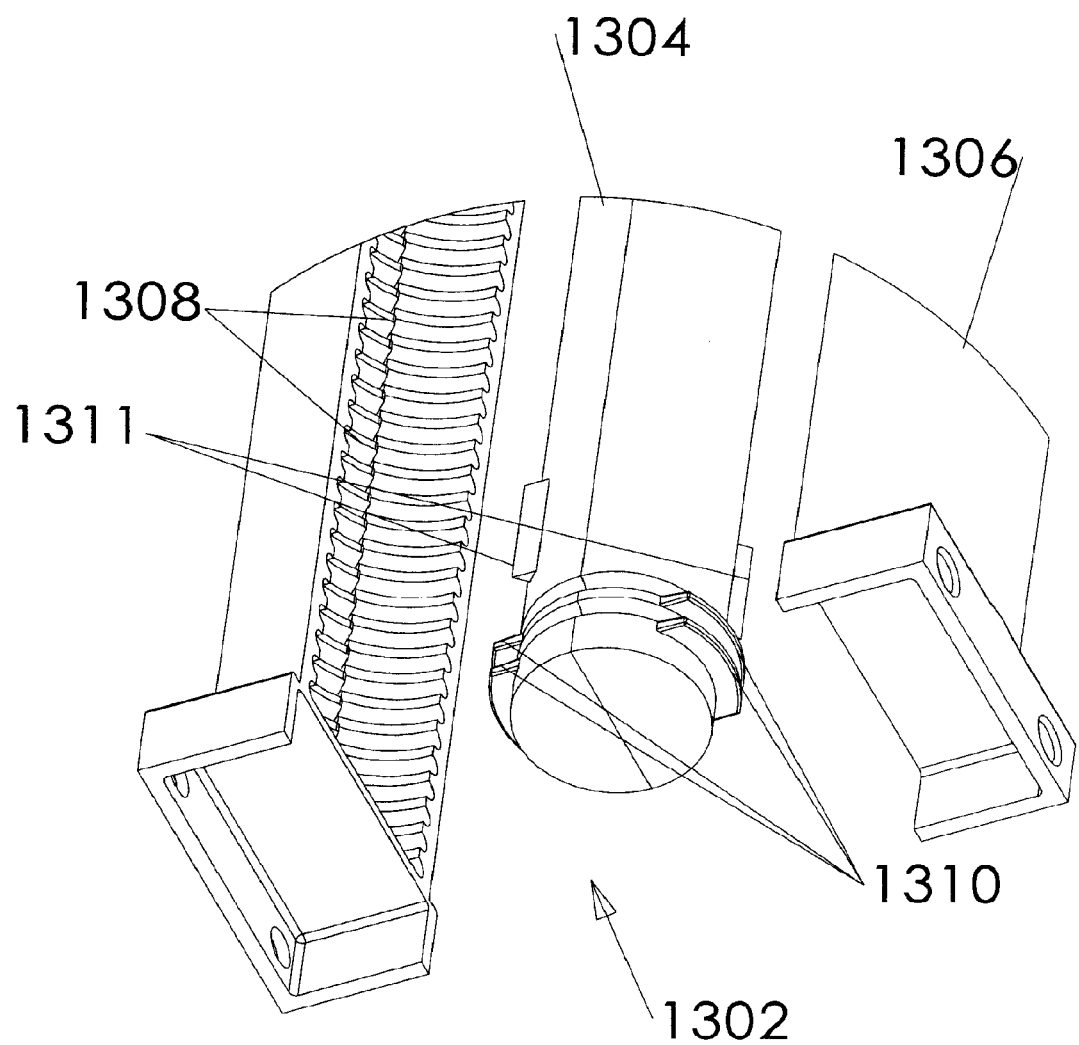
FIG. 13C illustrates an exploded isometric view of an alternative support strut according to some embodiments of the present invention.

FIG. 13A illustrates an isometric view of an alternative support strut 1302 according to some embodiments of the present invention. Support strut 1302 includes an inner strut 1304 and an outer strut 1306. Support strut 1302 is a round strut that uses a one-fourth turn to release interlocking threads. FIGS. 13B and 13C illustrate exploded isometric views of support strut 1302 according to some embodiments of the present invention. One or more teeth 1310 formed on inner strut 1304 interlock with corresponding ribs 1308 formed on an inner diameter of outer strut 1306. When inner strut 1304 is rotated slightly, such as, for example, a one-quarter turn, teeth 1310 disengage and/or clear ribs 1308, permitting inner strut 1304 to be slid up or down within outer strut 1306, so as to adjust the length of support strut 1302. A rib 1311 on inner strut 1304 prevents over-rotation of inner strut 1304 and prevents inner strut 1304 from being removed from outer strut 1306. Each strut 1304, 1306 may be formed from two half-shells ultrasonically welded together for production.

In addition to support struts 102, 1302, various other support strut alternatives may be used according to some embodiments of the present invention. For example, a support strut may be used that off-weights the foot via a cable, strap, or rope. The cable, strap or rope may attach to a top strut and a bottom strut, and a hook, knob, latch, buckle, or other engagement mechanism may secure the cable, strap or rope when the support strut has been adjusted to a desired overall length by extending or retracting the top strut with respect to the bottom strut. Weight from the supported limb may be transferred to the cable, strap or rope in the form of a tension force. In some cases, one or more pulleys may be used to reverse the direction of a tension force.

Other possible alternatives of support struts may include a support strut with a top and bottom strut, the length of the top and bottom struts at least partially overlapping at a desired support strut length. Such a support strut may be adjusted to a desired length, and may include a latch or strap at the top of the bottom strut and at the bottom of the top strut. Once the support strut has been adjusted to the desired length, the latches or straps may be secured or tightened to prevent the bottom strut from sliding relative to the top strut, so as to carry a load applied to the support strut. For example, a strap may be inserted through openings on the bottom strut and the top strut and wrapped around the bottom and top struts and tightened.

Yet other possible alternatives of support struts may include a support strut with a twist-tightened joint, such as, for example, a joint commonly found in camera stands. Such a support strut may include an outer piece with a collar and an inner piece that slides within the outer piece until the inner and outer pieces are twisted together to tighten them. A telescoping-type joint may be used to permit the length of the support strut to be adjusted. Such a support strut employs friction to prevent further sliding of the inner strut with respect to the outer strut once the joint has been tightened with adequate torque.

According to yet other alternative embodiments of the present invention, a hydraulic joint may be used to vary the length of a support strut. Such a support strut may include an outer and an inner strut, and the outer and inner struts may be coupled via a hydraulic joint. For example, a maximum length or displacement may be selected and/or fixed via graduated notches or pins. Then, a noncompressible fluid may be stored in a reservoir, and may be inserted between the inner and outer struts until the maximum length or displacement has been reached. As one possible alternative hydraulic strut, a compressible fluid may be stored between the inner strut and the outer strut in a compressed or shortened state; the inner and outer struts may then be released and the compressible fluid permitted to expand until the inner and outer struts slide in opposite directions to a desired length.

Support struts of variable length, such as support struts 102 and 1302, permit the same strut to fit limbs of different sizes. However, according to some embodiments of the present invention, one or more struts may be customized with a specific and/or predetermined fixed length based on the anatomic characteristics of a particular person. For example, embodiments of the present invention may be constructed to replace the limb of an amputee, such as during the time when another or permanent limb is being designed or constructed.

Figure 14A:
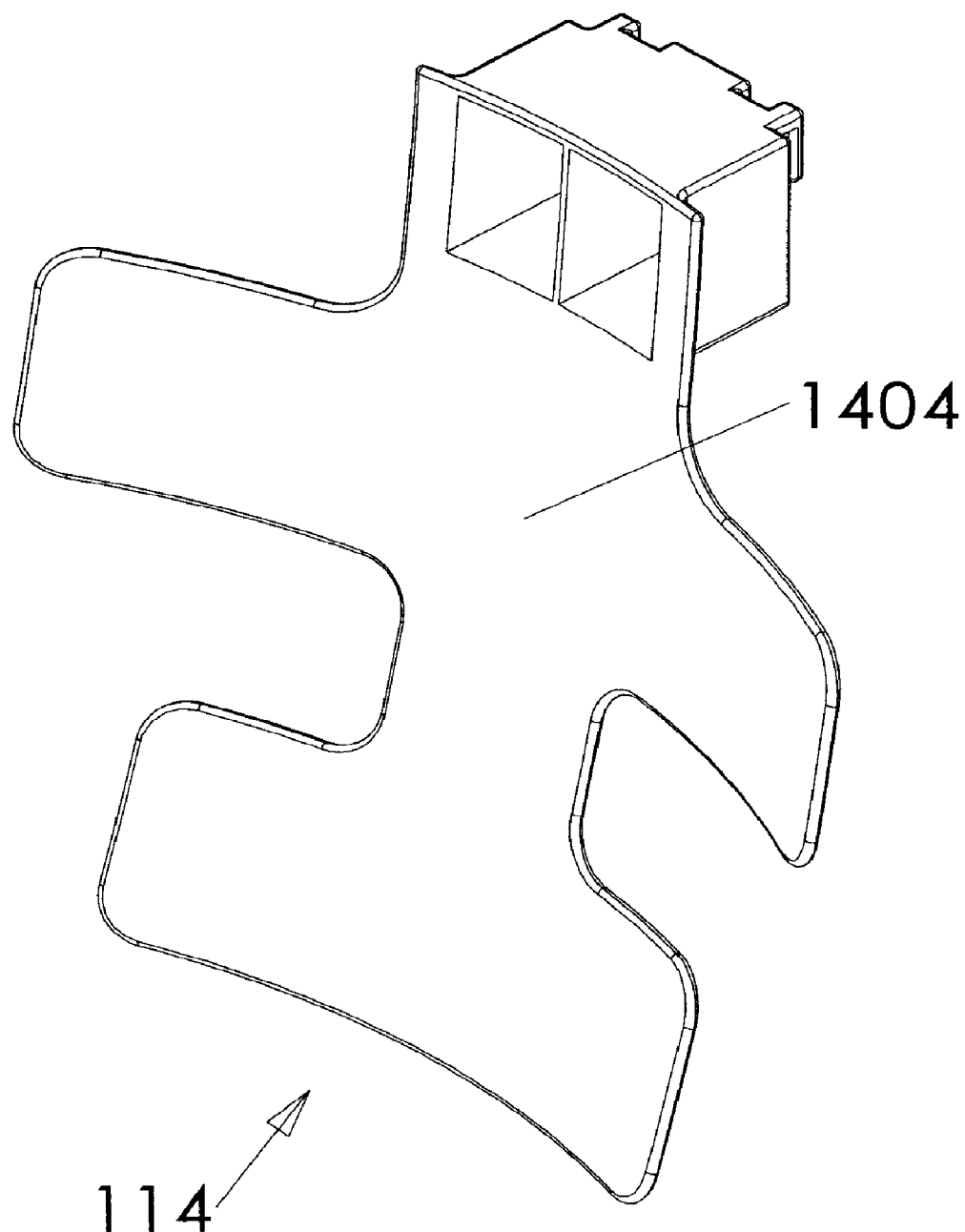
FIG. 14A illustrates an isometric view of a sleeve attachment according to some embodiments of the present invention.
Figure 14B:
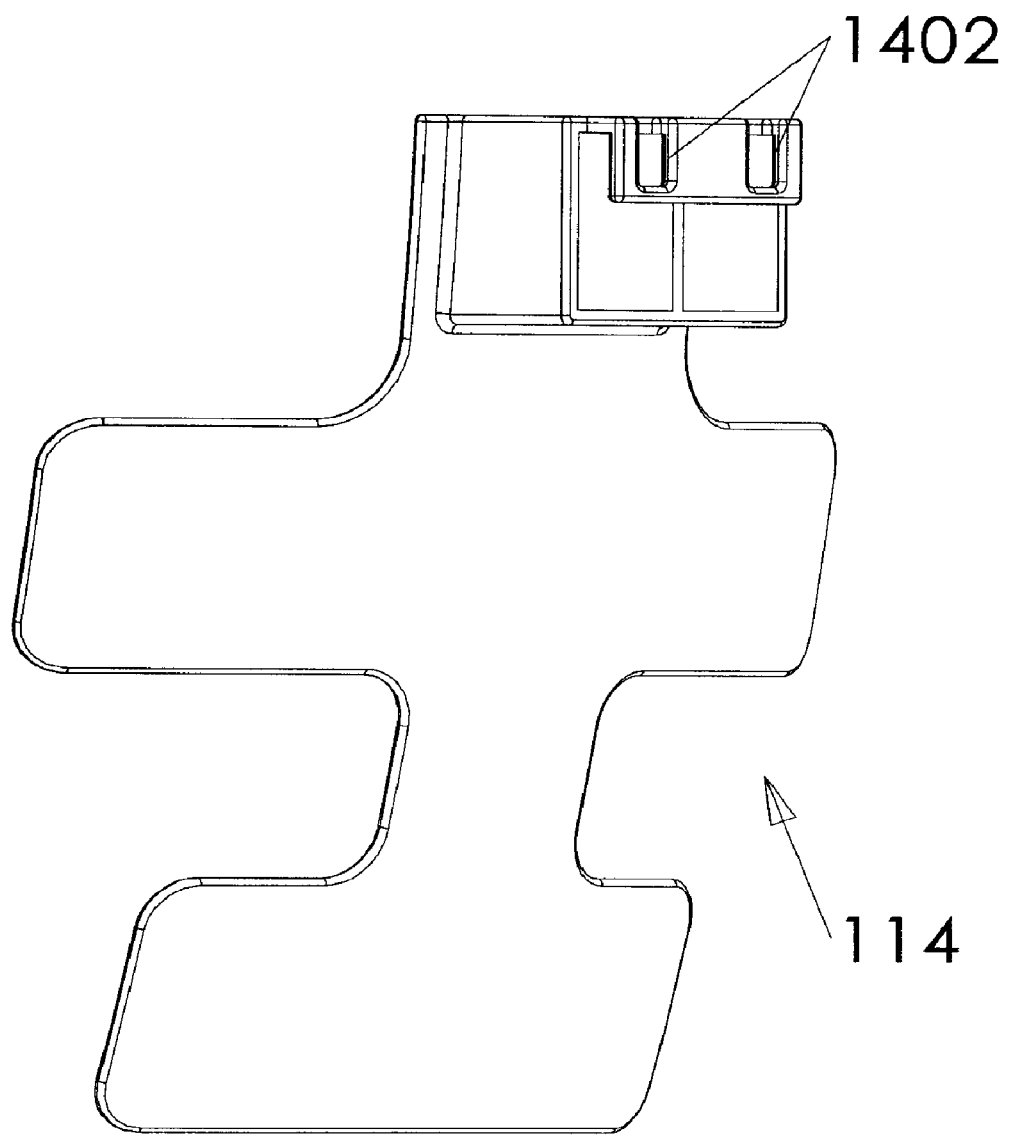
FIG. 14B illustrates a different isometric view of a sleeve attachment according to some embodiments of the present invention.

FIGS. 14A and 14B illustrate isometric views of sleeve attachment 114 according to some embodiments of the present invention. Sleeve attachment 114 is configured to snap onto top 1102 of inner strut 122, and is preferably flexible enough to conform to the leg when applied and when pulled tight by a securing strap. Snap slots 1402 of sleeve attachment 114 interface and/or lock onto snap hooks 1222 of top 1102, and sleeve attachment 114 rests within sleeve attachment pocket 1220. Hook tape may be applied to a surface 1404 of sleeve attachment 114 for improved coupling with sleeve 116, 400, or 402. In some cases, hook tape may be applied to surface 1404 with pressure sensitive adhesive. Snap slots 1402 may also serve as clearance holes for support strut straps. Sleeve attachment 114 may possess an initial curvature to assist in conforming to the leg.

FIG. 15A illustrates a front perspective view of off-weighting device 100 showing support struts angled to fit a calf of minimum width, and FIG. 15B illustrates a front perspective view of an off-weighting device showing support struts angled to fit a calf of maximum width, according to some embodiments of the present invention. As described above with respect to FIG. 5, off-weighting device 100 may be designed for support struts 102 to tilt in and out to adjust for various calf widths. Based upon anthropometric data, the calf width is estimated to vary from 3.75 inches to 5.25 inches. With a total thickness of some embodiments of sleeve 116 of approximately 0.125 inches following the compression of the foam, the total width of the calf may vary from 4 inches to 5.5 inches; however, the exact amount of compression of the leg is not known. Off-weighting device 100 may have a nominal width between struts 102 of 4.73 inches. A clearance between struts 102 and foot plate 110 may allow for tilting. A minimum width between sleeve attachments 114 may be approximately 3.73 inches, as illustrated in FIG. 15A. A maximum width may be 5.73 inches when support struts 102 are fully retracted, as illustrated in FIG. 15B. According to some embodiments of the present invention, larger calf widths may be accommodated as support struts 102 are lengthened. Support struts 102 may also exhibit a degree of flexibility so as to permit the accommodation of larger calf widths.

Figure 16:
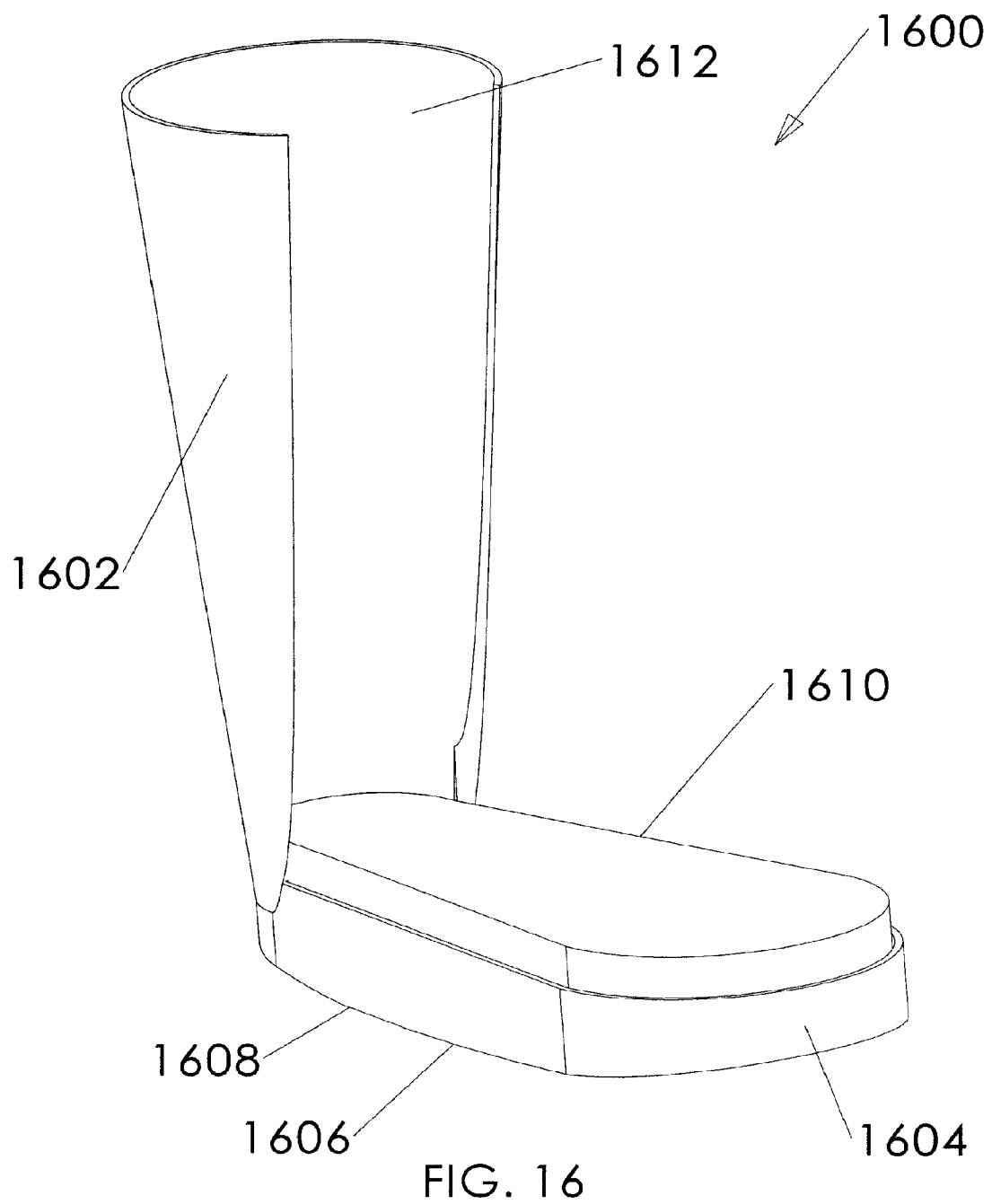
FIG. 16 illustrates an isometric view of an alternative off-weighting device according to some embodiments of the present invention.

FIG. 16 illustrates an isometric view of an alternative off-weighting device 1600 according to some embodiments of the present invention. Off-weighting device 1600 may remove weight from the foot and ankle and transfer that weight to the calf area of the leg. Off-weighting device 1600 may utilize a boot- or shoe-type cast having a tapered foam sleeve, such as, for example, sleeve 116, 400, or 402, placed around the calf. Sleeve 116, 400, or 402 provides an interface from the weight-bearing portion of the cast to the leg, reducing weight application to the foot and ankle. Sleeve 116, 400, or 402 and cast configuration may also minimize shearing around a wound site through restriction of movement. Off-weighting device 1600 may provide for off-weighting by transferring the load from the ground into the calf instead of carrying the load through the foot and ankle. Off-weighting device 1600 may incorporate a foot assembly 1604 having an inclined rocker sole 1608 with an inclined tread 1606 to move loads from the forefoot to the heel. Off-weighting device 1600 may also include a rigid structure 1602, such as a rigid plastic shell structure or rigid boot structure, for the boot housing, and/or a foam pad 1610 and/or wrap for the foot and/or leg to provide comfort. Rigid shell structure 1602 may alternatively be formed of a fiberglass or similar material. An inside surface 1612 of rigid shell structure 1602 may be configured to attach to an outside surface of sleeve 116, 400, or 402; for example, sleeve 116, 400, or 402 may be coupled to inside surface 1612 via a hook-and-loop attachment system.

Figure 21:
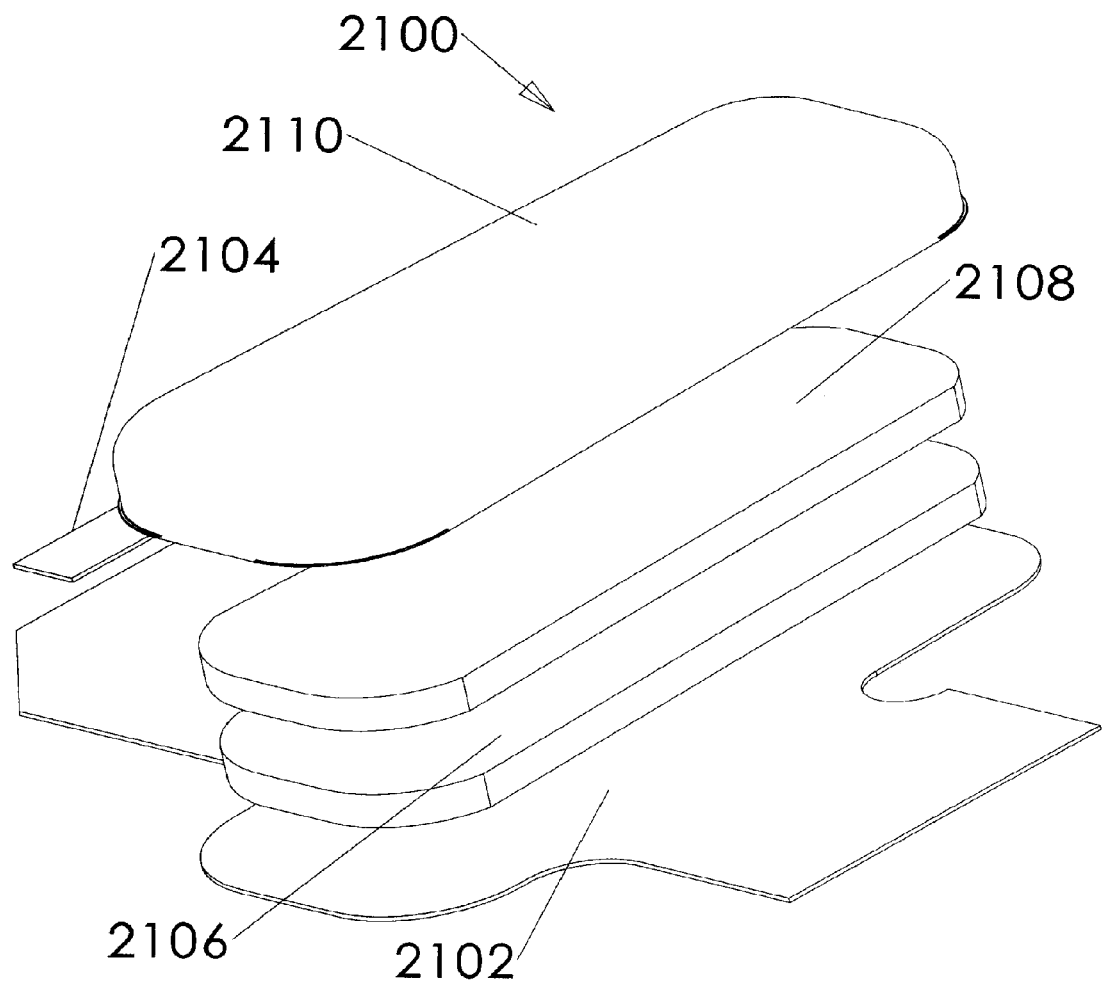
FIG. 21 illustrates an isometric view of a foot pad according to some embodiments of the present invention.

Once a user has removed off-weighting device 100 from any packaging, applied sleeve 116, 400, or 402 to the leg with the top of sleeve 116, 400, or 402 at the largest portion of the calf, rotated foot assembly 104 to an assembled position (or rotated struts 102 to a vertical position), and adjusted toe extender 106 and/or heel extender 302 to accommodate the foot size, the user may then rest the foot on foot assembly 104. Alternatively, the user may rest the foot on and/or within a foot pad 2100, as depicted in FIG. 21. Such a foot pad 2100 may wrap around a user's foot, and may provide a higher degree of comfort. A bottom surface of foot pad 2100 may be configured to attach with top surface 514 of foot plate 110, such as, for example, via a hook-and-loop fastening system. Foot pad 2100 may include layers to increase comfort and stability. For example, foot pad 2100 may include a top layer 2110 to contact the user's foot, a middle layer 2108, and a bottom layer 2106. An outer wrap 2102 may be wrapped around layers 2106, 2108, and 2110 and the user's foot, and fastened to itself via a fastener 2104 such as, for example, a hook-and-loop type fastener.

Foot pad 2100 may provide support and comfort to the foot and create a protective wrap around the foot. According to some embodiments of the present invention, foot pad 2100 wraps around the entire foot and lower leg, adjusting for different lengths of feet through a folding over of the end of the wrap. Wrap 2102 and/or top layer 2110 may be created from a warp knit nylon foam material that provides a soft touch feel against the skin. According to some embodiments of the present invention, top layer 2110 wraps around middle layer 2108 and bottom layer 2106 and is joined to outer wrap 2102 via a means such as sewing or RF welding, thereby encompassing or capturing middle layer 2108 and bottom layer 2106. A soft foam pad middle layer 2108, equivalent to approximately a half inch of 4.35 pound HSSX7 material, may be used to support the bottom of the foot. The soft foam pad may then be reinforced by a bottom layer 2106 of stiffer foam. The bottom layer may be constructed, for example, of a half-inch layer of EV-50 foam, supplied by RAM Technologies, with a density of 3.1 pounds per cubic inch. Various other foams or cushioning materials may be used for layers 2106, 2108, 2110 to achieve varying levels of support and comfort. According to other embodiments of the present invention, foot pad 2100 allows for an open toe and lacks a wrap around the leg. Such embodiments may provide greater access to wounds for evaluation without removal of off-weighting device 100 and/or foot pad 2100. Foot pad 2100 may be assembled via sewing or through the use of radio frequency welding technologies. Seams of foot pad 2100 may be created such that the potential of pressure or rubbing against the foot are minimized.

Next, struts 102 are extended using the methods described above until top 1102 of support strut 102 is approximately one half inch above the top of sleeve 116, 400, or 402. Sleeve attachments 114 may then be affixed to each side of sleeve 116, 400, or 402 in line with the tibia. For example, sleeve attachments 114 are affixed to each side of sleeve 116, 400, or 402 via a hook-and-loop fastening system. Once sleeve attachments 114 have been affixed to sleeve 116, 400, or 402, a strap is fed through any strap holes, such as snap slots 1402, and tightened around sleeve attachments 114. Sleeve attachments 114 may then be locked and/or snapped over tops 1102 of support struts 102. Straps may be fed through any slots, such as strap slots 1224, and secured around the leg and struts 102. Straps may be wrapped around the leg and support struts 102 in such a fashion to assist in securing off-weighting device 100 to the user. The straps may be pre-threaded to inner strut 122 and/or strut latch 120, into which slots 1224 are molded to allow for assembly of the straps. Strapping around strut latch 120 may also provide additional force to keep strut latch 120 closed and to prevent inadvertent opening of strut latch 120. Next, straps may be secured around foot plate 110 and/or the foot. Heel support 112 may be installed and/or adjusted if desired. Finally, the height of support struts 102 may be adjusted up or down to provide more or less off-weighting as needed.

Manufacturing and/or assembling off-weighting device 100 may also be accomplished in a timely and cost-effective manner. An injection molding process may be used to make various plastic or other components of off-weighting device 100; for example, injection molding may be used to complete the assembly of support struts 102 and foot assembly 104. A support strut 102 may consist of two outer strut 118 pieces which may be welded together via a tongue and groove ultrasonic weld joint to provide excellent strength. Alternatively, outer strut 118 pieces may be secured together by screws, bolts, glue, nails, or other fastening mechanisms. Care should be taken during molding to ensure that no interferences exist that might impact the joint. Assembling foot assembly 104 may also be accomplished by welding foot plate 110 to stiffener 108 via a tongue-and-groove welding joint.

According to some embodiments of the present invention, a large portion of off-weighting device 100 assembly may be conducted through a series of snap fits. First, inner strut 122 may be inserted between outer struts 118; then, with support strut 102 at its lowest (retracted) position, one strut latch 120 may be installed on each side of outer struts 118 through openings 1014, 1016 in the side of outer strut 118. Latch lever 902 may then be attached by pulling the sides of latch lever 902 apart and snapping forked arms 1204 of latch lever 902 over lever interface pins 1202 on strut latches 120 and allowing pivot pins 1206 of latch lever 902 to seat into holes 1012 on the side of support strut 102.

Further assembly of off-weighting device 100 may be accomplished by attaching tread 304 to foot assembly 104 via pressure sensitive adhesive applied to tread 304. Hook tape may be added to a top 512 of foot plate 110 with pressure sensitive adhesive. Strut pivot 202 may be snapped into foot assembly 104, the orientation of the pivot ensuring that foot assembly 104 of off-weighting device 100 is capable of rotating into an assembled position for use in the field. Next, one support strut 102 may be snapped into each side of strut pivot 202, oriented such that latch lever 902 faces out from foot plate 110. Heel extender 302 may be snapped into the back side of foot assembly 104, and toe extender may be snapped into the front side of foot assembly 104. Finally, two attachment straps may be threaded through strap slots in support struts 102 on each side of off-weighting device 100, such that one strap is threaded through each set of slots. The final assembled off-weighting device 100 may be placed in a folded or storage position, as depicted in FIG. 2.

Figure 17:
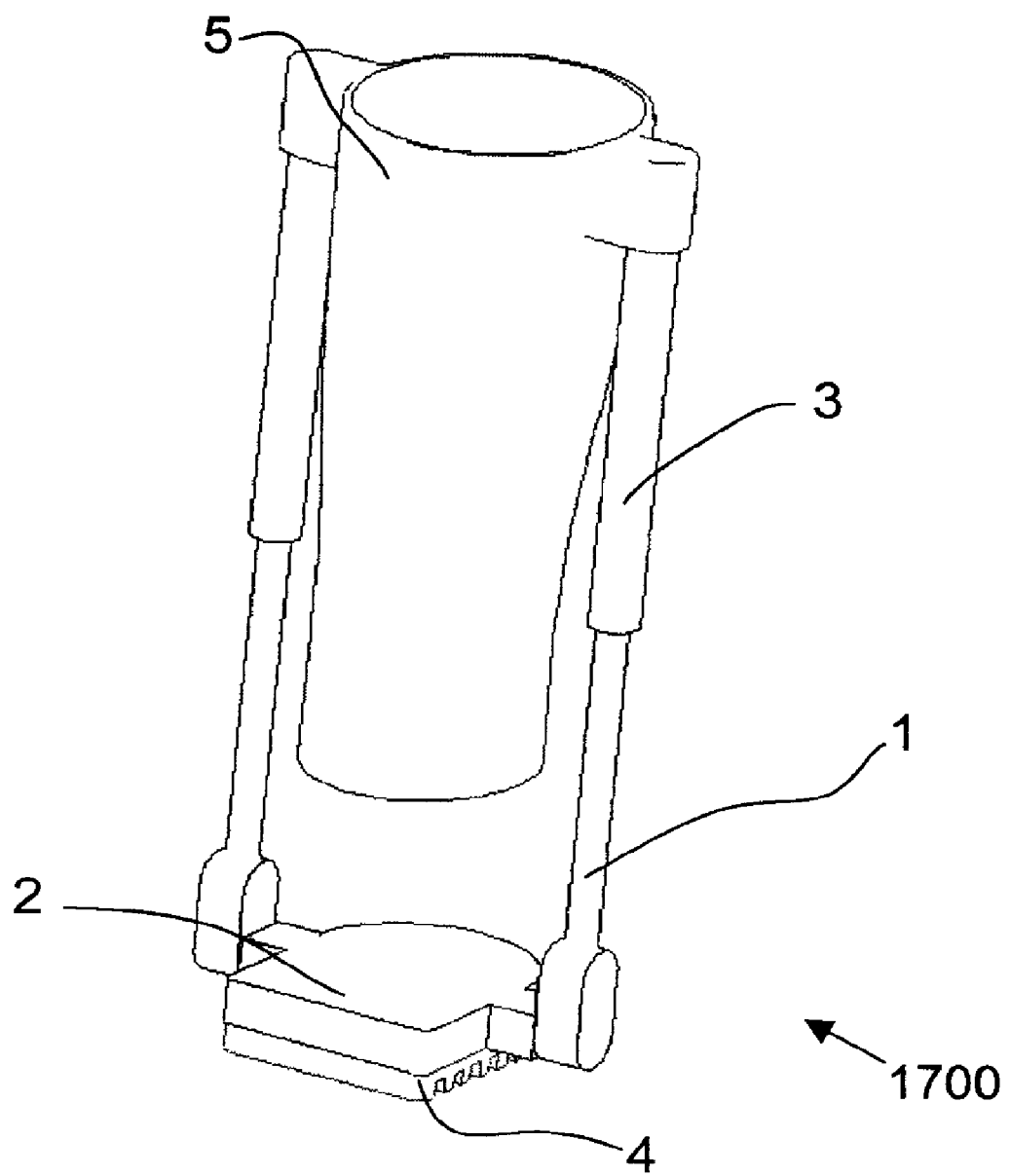
FIG. 17 illustrates an isometric view of an off-weighting device in an assembled position according to some embodiments of the present invention.
Figure 18:
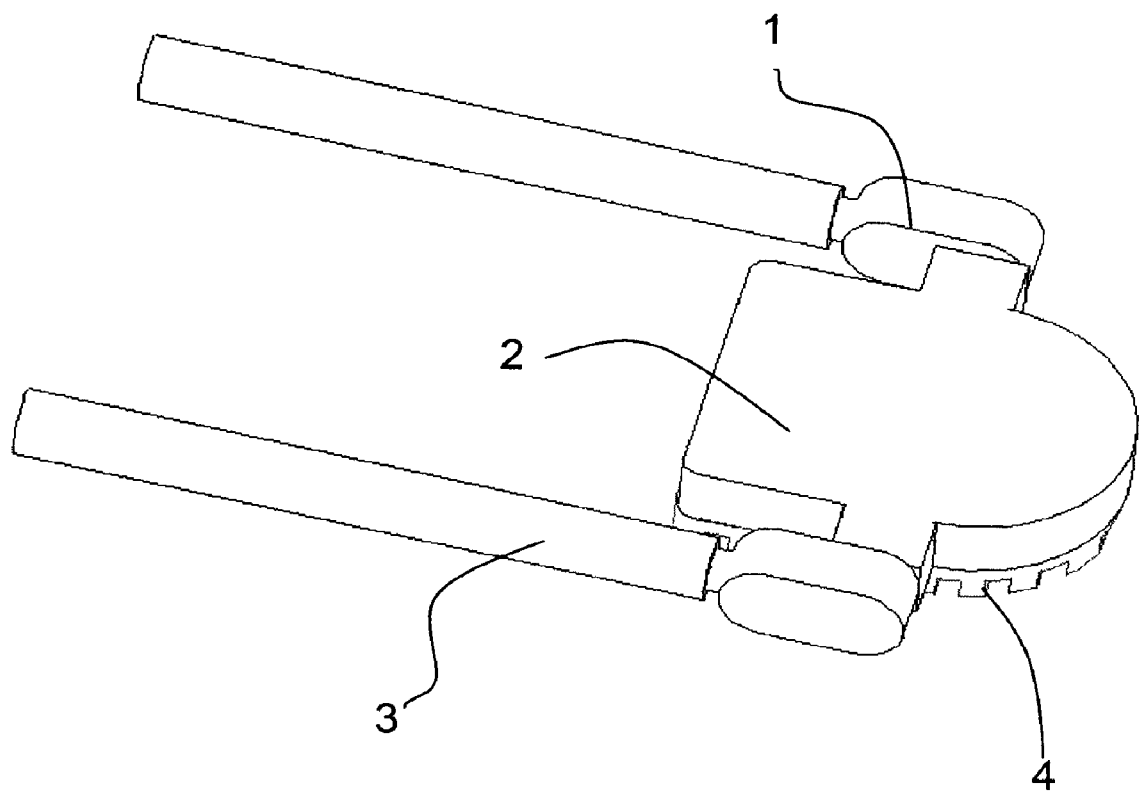
FIG. 18 illustrates an isometric view of an off-weighting device in a folded position according to some embodiments of the present invention.
Figure 19:
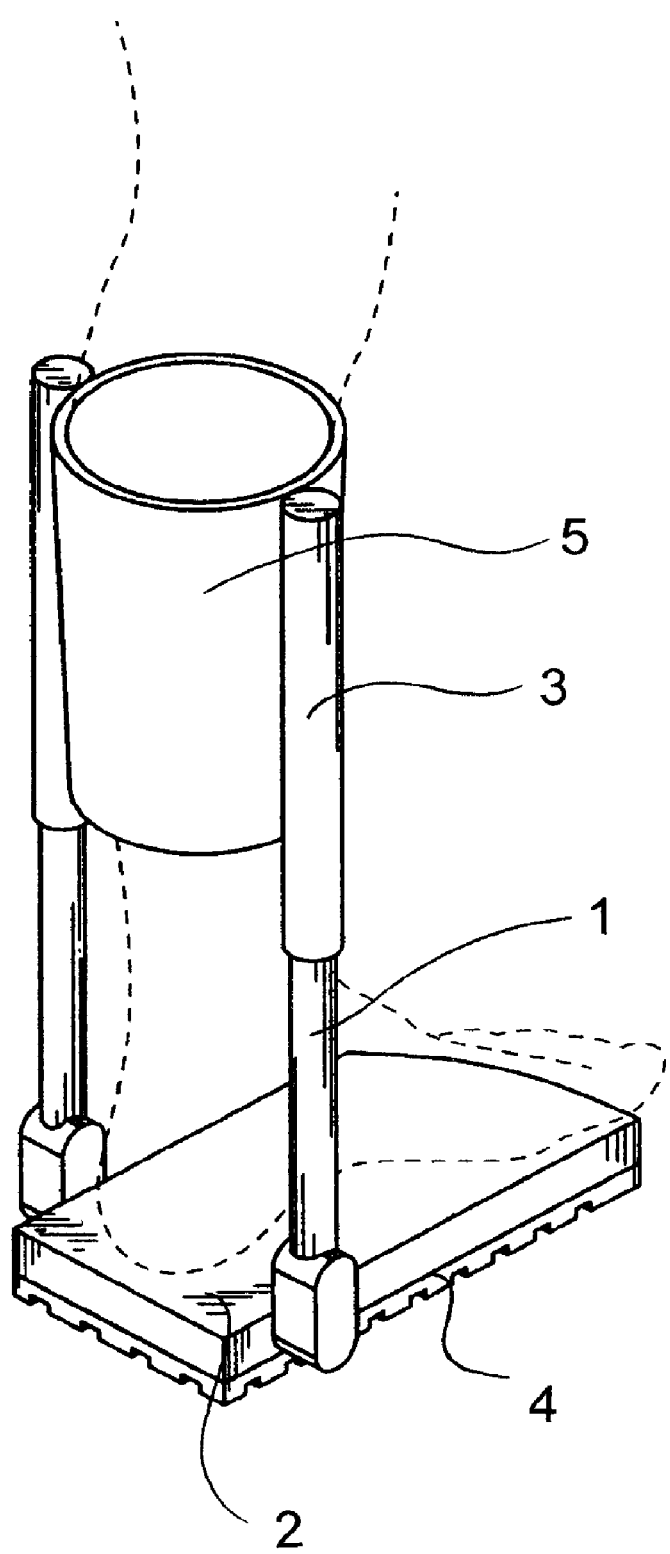
FIG. 19 illustrates an isometric view of an off-weighting device in an assembled position, applied to a leg according to some embodiments of the present invention.
Figure 20A:
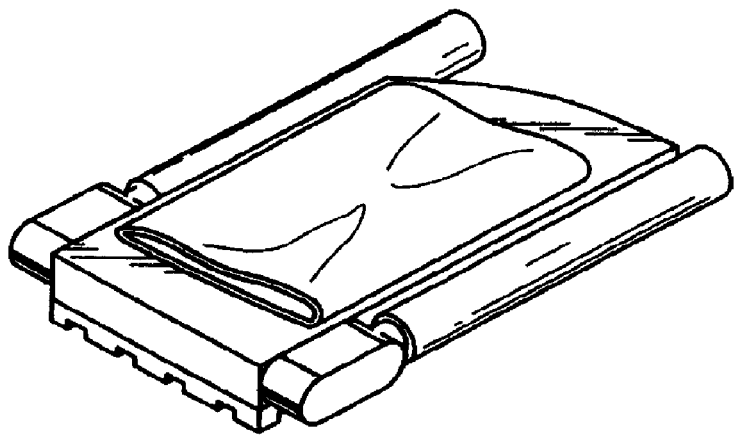
FIG. 20A illustrates an isometric view of an off-weighting device in folded position according to some embodiments of the present invention.
Figure 20B:
FIG. 20B illustrates a side perspective view of an off-weighting device in folded position according to some embodiments of the present invention.
Figure 20C:
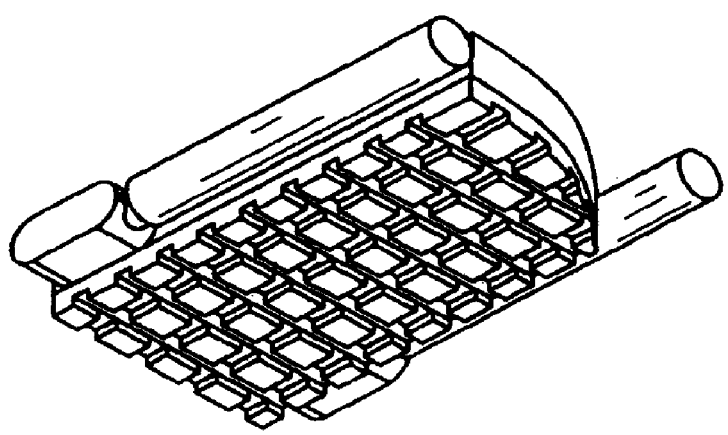
FIG. 20C illustrates another isometric view of an off-weighting device in folded position according to some embodiments of the present invention.

Referring now to FIGS. 17-20C, FIG. 17 illustrates an isometric view of an alternative off-weighting device 1700 in an assembled position according to some embodiments of the present invention. FIG. 18 shows off-weighting device 1700 in a folded position, and FIG. 19 shows off-weighting device 1700 in an assembled position, applied to a leg according to some embodiments of the present invention. FIGS. 20A-20C depict off-weighting device 1700 in a folded position according to some embodiments of the present invention.

Some embodiments of the present invention provide a compact and/or lightweight system as shown in FIG. 17. In such embodiments, off-weighting device 1700 is collapsed for storage as shown in FIG. 18. When applied, support struts 1 are rotated relative to a foot plate 2, from a horizontal to a vertical position. An upper strut 3 is then extended relative to a lower strut 1 to a preferred position dependent on the size and weight of the patient. Marks which are integral with the upper and lower struts, 3 and 1, provide guides for the adjustments. A sleeve 5 is shaped to a conical pattern and is wrapped around the lower leg of the patient from approximately one inch above the largest part of the calf to just above the ankle. The size of the sleeve 5 is adjusted dependent upon the patient. Hook and loop fasteners integral to the sleeve may be utilized to secure the sleeve to itself Alternative fastening means may also be utilized.

The components of off-weighting device 1700 may include a bladder/sleeve 5, which may provide the conforming surface between off-weighting device 1700 and the patient's leg. This creates the zone of total contact that distributes the load being transferred from the ground into the leg. Through the tapered design, the pressure on the leg is relieved when the patient is not applying load to the leg. This improves the long term comfort of the system. Bladder/sleeve 5 may need to allow for adjustment and be capable of being customized for each user (medical patient, war fighter, etc.) at the time of application. Reclosable fasteners, such as hook and loop tape, may be used to secure the bladder to itself after it is wrapped around the leg.

Off-weighting device 1700 may further include a structural support system responsible for carrying the load from the tread to the bladder/sleeve 5. Such a system may include lower struts 1, foot plate 2, and upper struts 3. Such a system may provide the necessary rigidity to create off-weighting and to carry side loads during ambulation. This structural strength must be balanced with the weight and size of the system. The support system may be easily deployed from a stored configuration into the functional layout with minimal effort. When collapsed for storage, the structural system may also provide a location for storing the bladder/sleeve 5.

Off-weighting device 1700 may further include a tread configured to provide traction and a level of cushioning when ambulating. Additional features of off-weighting device 1700 may include a heel support to prevent motion of the ankle, a moisture control material on the interior of the sleeve and a cover to enclose the foot and ankle region.

Embodiments of the present invention have been described for off-weighting a foot, ankle, and/or lower leg; however, off-weighting of a hand or wrist is also contemplated by embodiments of the present invention. According to such embodiments, a sleeve similar to sleeves 114, 400, 402 may be wrapped around an arm or forearm. Struts, for example struts similar to support struts 102, 1302, may be coupled to the sleeve on one end, such as, for example, via attachment mechanisms like sleeve attachments 114. The struts may be adjustable in length to fit arms of different sizes, similarly to struts 102, 1302. On the other end, such struts may be coupled with a support assembly, such as a plate or grip that performs a function for the hand similar to the function that foot assembly 104 and/or foot plate 110 performs for the foot. Such a hand off-weighting device may permit a user to perform a pushing motion despite an injured hand or wrist, by redirecting force applied by the arm through the off-weighting device, into the plate or grip, and ultimately into the element being pushed.

Embodiments of the invention have now been described in detail for purposes of clarity and understanding. However, it will be appreciated that certain changes and modifications may be practiced within the scope of the appended claims. Thus, although the invention is described with reference to specific embodiments and figures thereof, the embodiments and figures are merely illustrative, and not limiting of the invention. Rather, the scope of the invention is to be determined solely by the appended claims.

What is claimed is:

1. A system for limb off-weighting to reduce pressure and shear stress, the system comprising:
    a sleeve operable to wrap at least partially around a leg;
    a support strut coupled to the sleeve and operable to receive weight applied to the sleeve, wherein the support strut is extendable; and
    a foot assembly configured to extend under a foot and to support a bottom of the foot, wherein the foot assembly is pivotably coupled to the support strut and operable to receive the weight applied to the sleeve and transfer the weight to an underlying surface, and wherein the support strut pivots about the foot assembly from an upright position in which the support strut is substantially perpendicular to the foot assembly to a folded position in which the support strut is substantially parallel to the foot assembly.

2. The system of claim 1, wherein the sleeve is coupled to the support strut via a sleeve attachment.

3. The system of claim 2, wherein the sleeve is coupled to the sleeve attachment via a hook-and-loop closure.

4. The system of claim 1, wherein the support strut pivots about the foot assembly approximately ninety degrees from the upright position to the folded position.

5. The system of claim 1, wherein the support strut comprises an inner strut and an outer strut, the inner strut slidably coupled to the outer strut via a strut latch.

6. The system of claim 5, wherein the strut latch substantially prevents the inner strut from sliding relative to the outer strut in a closed position, and wherein the strut latch allows the inner strut to slide relative to the outer strut in an open position.

7. The system of claim 5, wherein the inner strut is coupled to the sleeve and the outer strut is coupled to the foot assembly.

8. The system of claim 1, wherein the support strut is retractable.

9. The system of claim 1, wherein the sleeve forms an open-ended conical shape.

10. The system of claim 1, wherein the sleeve is tailored for attachment to an area of the human body selected from the group consisting of: a thigh area and a calf area.

11. The system of claim 1, wherein the foot assembly provides traction during ambulation.

12. The system of claim 1, further comprising a heel support.

13. The system of claim 1, further comprising a foot pad.

14. The system of claim 1, wherein the foot assembly comprises an extender selected from the group consisting of: a heel extender and a toe extender.

15. The system of claim 1, wherein the sleeve comprises a bladder with chambers filled with air or other conformable material, wherein the conformable material may harden following application of the sleeve to the leg.

16. The system of claim 1, wherein the sleeve is perforated with a plurality of vent holes to improve air circulation for moisture and temperature management.

17. An apparatus for limb off-weighting, comprising:
a sleeve operable to wrap at least partially around a leg;
a support strut coupled to the sleeve and operable to receive weight applied to the leg, wherein the support strut is extendable; and
a foot assembly configured to extend under a foot and to support a bottom of the foot, wherein the foot assembly is pivotably coupled to the support strut and operable to receive the weight applied to the support strut and transfer the weight to an underlying surface, and wherein the support strut pivots about the foot assembly approximately ninety degrees from an upright position to a folded position.

* * * * *